(12) United States Patent
Klebba et al.

(10) Patent No.: US 10,604,782 B2
(45) Date of Patent: Mar. 31, 2020

(54) HIGH-THROUGHPUT FLUORESCENT SCREENING ASSAY FOR INHIBITORS OF GRAM-NEGATIVE BACTERIAL IRON UPTAKE

(71) Applicant: Kansas State University Research Foundation, Manhattan, KS (US)

(72) Inventors: Phillip E. Klebba, Manhattan, KS (US); Salete M. Newton, Manhattan, KS (US); Brittany L. Nairn, Burnsville, MN (US); Mathew Hanson, Silverton, OR (US)

(73) Assignee: Kansas State University Research Foundation, Manhattan, KS (US)

( * ) Notice: Subject to any disclaimer, the term of this patent is extended or adjusted under 35 U.S.C. 154(b) by 0 days.

(21) Appl. No.: 15/739,065

(22) PCT Filed: Jul. 1, 2016

(86) PCT No.: PCT/US2016/040815
§ 371 (c)(1),
(2) Date: Dec. 21, 2017

(87) PCT Pub. No.: WO2017/004577
PCT Pub. Date: Jan. 5, 2017

(65) Prior Publication Data
US 2018/0187236 A1 Jul. 5, 2018

Related U.S. Application Data

(60) Provisional application No. 62/188,238, filed on Jul. 2, 2015, provisional application No. 62/343,577, filed on May 31, 2016.

(51) Int. Cl.
*C12Q 1/02* (2006.01)
*C07K 14/21* (2006.01)
*C12N 1/20* (2006.01)

(52) U.S. Cl.
CPC ............ *C12Q 1/025* (2013.01); *C07K 14/212* (2013.01); *C12N 1/20* (2013.01); *G01N 2333/212* (2013.01); *G01N 2458/00* (2013.01)

(58) Field of Classification Search
CPC .. C12Q 1/025; C07K 14/212; G01N 2458/00; G01N 2333/212; C12N 1/20
See application file for complete search history.

(56) References Cited

U.S. PATENT DOCUMENTS

| | | | | |
|---|---|---|---|---|
| 2005/0287070 A1* | 12/2005 | Klebba | ................... | A61K 49/20 424/9.1 |
| 2012/0208744 A1* | 8/2012 | Postle | ................... | A01N 37/46 514/2.8 |

OTHER PUBLICATIONS

Yep et al., (MBIO.asm.org. vol. 5, Issue 2. e01089-13. Published Feb. 25, 2014) (Year: 2014).*

(Continued)

*Primary Examiner* — Jana A Hines
(74) *Attorney, Agent, or Firm* — Hovey Williams LLP

(57) ABSTRACT

A cell-based assay for identifying a compound that inhibits iron transport in Gram-negative bacteria, engineered bacterial cells, and kits for conducting the same. The assay involves contacting a candidate compound with an engineered Gram-negative bacteria in the presence of iron for a sufficient period of time, exposing the reaction solution to an energy source to generate the detectable signal, and detecting changes in the detectable signal in the reaction solution over time. The engineered Gram-negative bacteria comprises an iron transport protein on its outer membrane that comprises an amino acid residue that has been engineered with a detectable label that generates a detectable signal. The changes in the detectable signal in the assay system over time correspond to the effect of the candidate compound on iron transport in the Gram-negative bacteria.

25 Claims, 13 Drawing Sheets

(56) References Cited

OTHER PUBLICATIONS

Figure 1:
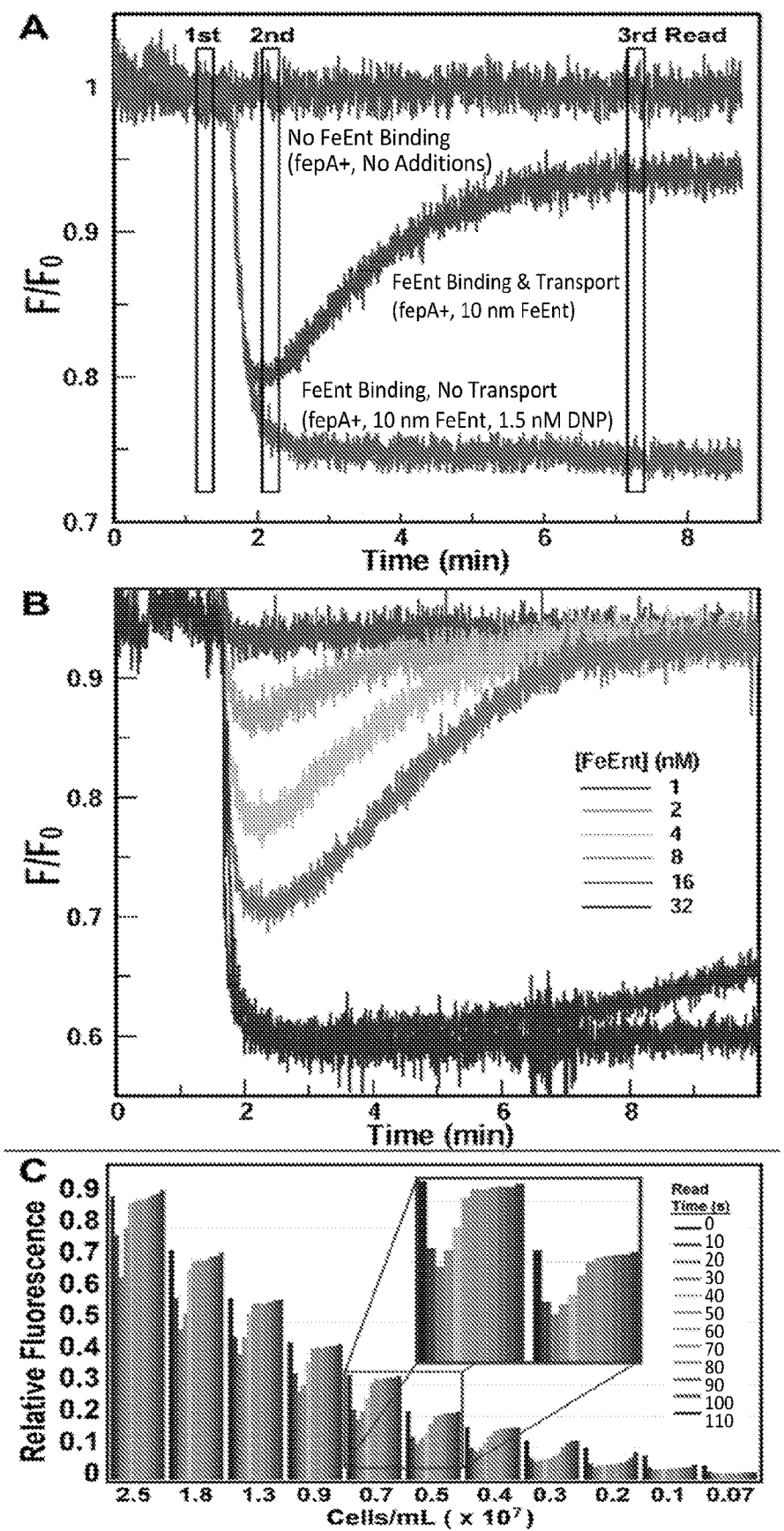

The International Search Report and Written Opinion dated Sep. 16, 2016, in PCT/US2016/040815, filed on Jul. 1, 2016.

Jordan, Lorne D. "Energy-dependent motion of TonB in the Gram-negative bacterial inner membrane," PNAS, Jul. 9, 2013, pp. 11553-11558; vol. 110, No. 28.

Kirkham, Lee-Ann S. "A practical method for preparation of pneumococcal and nontypeable Haemophilus Influenzae inocula that preserves viability and immunostimulatory activity," BMC Research Notes 2013. 6:552.

Smallwood, Chuck R. "Concerted loop motion triggers induced fit of FepA to ferric enterobactin," J. Gen. Physical, vol. 144, No. 1, 71-80, The Rockefeller University Press.

Yep, Alejandra "Inhibitors of TonB Function Identified by a High-Throughput Screen for Inhibitors of Iron Acquisition in Uropathogenic *Escherichia coli* CFT073," mBio Mar./Apr. 2014 vol. 5. Issue 2. mbio.asm.org.

Bjarnason, Jaime "Genomic Profiling of Iron-Responsive Genes in *Salmonella enterica* Serovar Typhimurium by High-Throughput Screening of a Random Promoter Library," Journal of Bacteriology, Aug. 2003, pp. 4973-1982, vol. 185, No. 16, American Society for Microbiology.

\* cited by examiner

A

B

HIGH-THROUGHPUT FLUORESCENT SCREENING ASSAY FOR INHIBITORS OF GRAM-NEGATIVE BACTERIAL IRON UPTAKE

CROSS-REFERENCE TO RELATED APPLICATIONS

The present application is the U.S. National Stage of International Patent Application No. PCT/US2016/040815, filed Jul. 1, 2016, which claims the priority benefit of U.S. Provisional Patent Application Ser. No. 62/188,238, filed Jul. 2, 2015, and Ser. No. 62/343,577, filed May 31, 2016, both entitled HIGH-THROUGHPUT FLUORESCENT SCREENING ASSAY FOR INHIBITORS OF GRAM-NEGATIVE BACTERIAL IRON UPTAKE, each of which is incorporated by reference in its entirety herein.

FEDERALLY SPONSORED RESEARCH OR DEVELOPMENT

This invention was made with government support under grant no. 1R21AI115187-01A1 awarded by the Department of Health and Human Services, National Institutes of Health. The government has certain rights in the invention.

BACKGROUND OF THE INVENTION

Field of the Invention

The present invention relates to assays for screening candidate compounds as inhibitors of iron transport in Gram-negative bacteria.

Description of Related Art

Iron acquisition is vital for bacteria from its role in energy production and DNA synthesis to intermediate metabolism, oxygen detoxification, and nitrogen fixation. In the host environment bacterial pathogens must acquire iron to proliferate. Their primary mechanism is secretion of siderophores that chelate ferric iron. Ferric enterobactin (FeEnt; 720 Da) utilizes FepA, an outer membrane protein that binds and internalizes it by active transport. The detailed mechanism of FeEnt transport through FepA remains uncertain, but the process is controlled by TonB. Active transport across the outer membrane poses an energetic challenge: how does accumulation occur in a membrane containing open porin channels (e.g., OmpF) that preclude an electrochemical gradient? TonB presumably overcomes this problem by transferring energy from the IM to the outer membrane, that facilitates FeEnt passage through FepA. The TonB C-terminus adsorbs to a conserved site known as the "TonB box" at the N-terminus of TonB-dependent transporters (TBDT) like FepA, and this association is the basis of energy transfer. After FeEnt passes into the periplasm it binds to FepB, which delivers it to the FepCDG ABC-transporter in the IM, that hydrolyzes ATP as it transports FeEnt into the cytoplasm.

Antibiotic resistance among various bacterial pathogens continues to be a major health concern. Recent efforts have focused on certain bacteria such as Carbapenem-resistant Enterobacteriaceae (CRE), and other Gram-negative pathogens (*Klebsiella pneumoniae*, *Acinetobacter* species, *Pseudomonas aeruginosa*, and *Enterobacter* species).

SUMMARY OF THE INVENTION

The present invention is broadly concerned a cell-based assay for identifying a compound that inhibits iron transport in Gram-negative bacteria. The assay comprises creating a reaction solution by contacting a candidate compound with an engineered Gram-negative bacteria in the presence of iron for a sufficient period of time, exposing the reaction solution to an energy source to generate the detectable signal; and detecting changes in the detectable signal in the reaction solution over time. The engineered Gram-negative bacteria comprises an iron transport protein on its outer membrane that comprises an amino acid residue that has been engineered with a detectable label that generates a detectable signal. The changes in the detectable signal in the assay system over time correspond to the effect of the candidate compound on iron transport in the Gram-negative bacteria. The reaction solution is generally created by contacting the candidate compound with the engineered Gram-negative bacteria in a reaction vessel. A source of iron is added to the reaction vessel, and incubated with the candidate compound with engineered Gram-negative bacteria in the vessel for a period of time. As described in more detail below, the assay is monitored over time and various readings are taken of the detectable signal at various time points (i.e., before addition of iron, after addition of iron, and after potential recovery/transport).

Correspondingly, the disclosed invention is concerned with spectrofluorimetric methods that can be used for high-throughput screening (HTS) to measure TonB-dependent FeEnt iron uptake through fluorescently labeled FepA in microtiter plates. The assay may screen for inhibitors, with high Z-factors that demonstrated sensitivity, flexibility and reproducibility. FeEnt uptake can be observed with this microtiter test to identify inhibitors of TonB-dependent action. The assay monitors FeEnt uptake through FepA in living engineered bacteria, by monitoring fluorescence quenching that occurs upon binding of FeEnt, and then un-quenching as the bacteria deplete it from solution by transport. The assay works like a molecular switch that is on in the presence of TonB activity, and off in its absence. The assay can be carried out in 96-, 384-, or 1536-well microtiter plates, in a variety of conditions, with Z factors of 0.8-1.0. TonB-dependent iron transport is energy dependent, and the inhibitory effects of known metabolic inhibitors were readily detected by the assay and validate its applicability. Because iron acquisition is a determinant of bacterial pathogenesis, HTS with this method may identify inhibitors that block TonB function, and constitute novel therapeutics against infectious disease caused by Gram-negative bacteria.

The invention is also concerned with kits for conducting a cell-based assay to identify a compound that inhibits iron transport in Gram-negative bacteria. The kits generally comprise an engineered Gram-negative bacteria comprising an iron transport protein on its outer membrane, that has been engineered with a detectable label that generates a detectable signal. A source of iron may optionally be provided in the kit (or it can be obtained from a third party or otherwise provided on the user's end). The kit will also include instructions for creating a reaction solution with the engineered Gram-negative bacteria, source of iron, and a candidate compound(s). The kit will also include instructions for exposing the reaction solution to an energy source to generate the detectable signal, along with instructions for detecting changes in the detectable signal in the reaction solution over time to determine the effect of the candidate compound on iron transport in the Gram-negative bacteria. In some embodiments, the engineered Gram-negative bacteria may be provided with the kit in cryopreserved form. In such case, the kit may further comprise instructions for initial thawing of the bacteria for use in the assay.

Also described herein is an isolated *Acinetobacter baumannii* comprising a genetically-engineered cysteine substitution in its FepA protein at residue 278, 561, or 664, and a fluorophore covalently attached to the substituted cysteine residue. The engineered bacteria can be used in cell-based assays to identify compounds that inhibit iron transport by the bacteria cells.

BRIEF DESCRIPTION OF THE DRAWINGS

FIG. 1 shows the results of fluorescence spectroscopic measurement, wherein (A) is a graph showing responses observed in fluorescently labeled bacteria in the absence of FeEnt, during FeEnt binding only, and in response to FeEnt binding and transport, (B) is a graph showing the concentration dependence of FeEnt binding and transport (graph shows a single experiment that was representative of many other trials), and (C) is a graph showing the relationship between cell density and assay time in microtiter plates;

FIG. 2 shows assay durability, reproducibility, and Z Factors, wherein (A) is a graph showing cell stability during the assay, (B) and (C) are graphs showing the Z-factors in control experiments, and (D) is a graph showing Z-factor dependence on cell density;

FIG. 3 is a graph showing responses observed in fluorescently labeled bacteria in SLM fluorescence spectroscopic assay adapted to 384-well format, wherein the graph data points are the average of three replicates and representative of multiple experiments;

FIG. 4 compares the Z' scores among plates and the range of percent inhibition of each compound, wherein (A) is a graph showing Z' scores across all plates by ID number, and (B) is a graph showing percent inhibition of the compounds;

FIG. 5 is a list of the structures and names of the top 20 candidate TonB inhibitors following primary screening;

FIG. 6 shows the results of secondary siderophore nutrition tests and colicin killing assays reveals inhibitors of TonB, wherein (A) shows images of exemplary compounds with inhibiting phenotypes compared to the untreated bacteria based on siderophore nutrition tests for FeEnt and Fc, and (B) is a graph depicting the % survival of bacteria in the presence of colicin B and the compound based on colicin B killing assays;

FIG. 7 shows the evaluation of ΔfepA for utilization of FeEnt by *A. baumannii*, wherein (A) is a graph showing growth of WT and ΔfepA in MOPS minimal media plus or minus 100 μM apoferrichrome A, (B) is a graph showing growth of WT and ΔfepA in MOPS plus or minus 1 μM FeEnt, (C) is an image showing siderophore nutrition test with WT *A. baumannii* and ΔfepA following growth in Nutrient broth and plating in MOPS minimal media top agar containing 100 μM apoferrichrome A (representative of three separate images), (D) is an image showing FeEnt nutrition test with WT *A. baumannii*+pWH1266, ΔfepA+pWH1266, ΔfepA+pfepA, and ΔfepA+p2682profepA following growth in Nutrient broth and plating in MOPS minimal media top agar containing 100 μM apoferrichrome A (representative of three separate images), (E) is a graph showing the accumulation of $^{59}$FeEnt over time course of 45 min by WT *A. baumannii*+pWH1266, ΔfepA+pWH1266, and ΔfepA+pfepA following growth in Nutrient broth (consolidated from two separate experiments in triplicate), and (F) is a graph showing transport of $^{59}$FeEnt after 5 s and 1 min incubation with WT *A. baumannii* or ΔfepA following growth in MOPS minimal media (consolidated from two separate experiments in triplicate);

FIG. 8 is a model of AbaFepA revealing homology with EcoFepA and selection of amino acids for Cys substitution;

FIG. 9 shows that Cys substitution mutants in AbaFepA label with FM and display differential impact on FeEnt transport, wherein (A) show images of *A. baumannii* ΔfepA expressing the mutant FepA constructs, using fluorescent imaging (top) and Coomassie staining (bottom), (B) shows images of FeEnt nutrition test with wild-type *A. baumannii*+pWH1266, ΔfepA+pWH1266, ΔfepA+pfepA, and ΔfepA+pfepA with Cys substitutions following growth in Nutrient broth and plating in MOPS minimal media top agar containing 100 μM apoferrichrome A (image represents one of three separate experiments), and (C) is a graph depicting mutant strains that display at least 30% FeEnt transport when compared to WT untreated (data are consolidated from 2-3 experiments performed in triplicate);

FIG. 10 shows the detection of FeEnt transport in *A. baumannii* by fluorescence spectroscopy, wherein (A) is a graph of normalized fluorescence (final fluorescence volts/starting fluorescence volts; F/F0) of *A. baumannii* ΔfepA+pfepA-Cys mutants labeled with 5 μM FM followed by incubation with 10 nM FeEnt at 100 s and tracking fluorescence volts over time (consolidated data from three separate experiments), (B) is a graph of normalized fluorescence of *A. baumannii* ΔfepA+pfepA-5278C labeled with 5 μM FM followed by incubation with varying concentrations of FeEnt at 100 s and tracking fluorescence volts over time (consolidated data from two separate experiments), and (C) is a graph of normalized fluorescence of *A. baumannii* ΔfepA+pfepA-5278C labeled with 5 μM FM followed by incubation for 15 min with CCCP prior to SLM and then using 10 nM FeEnt at 100 s and tracking fluorescence volts over time (consolidated data from two separate experiments);

FIG. 11 shows fluorescence spectroscopy of *A. baumannii* ΔfepA+pfepA control, wherein (A) is a representative graph showing raw fluorescence volts comparing FM-labeled ΔfepA+pfepA and ΔfepA+pfepA-S278C plus 40 nM and 10 nM FeEnt, respectively, at 100 s, (B) is a graph showing normalized fluorescence of *A. baumannii* ΔfepA+pfepA labeled with FM followed by incubation with 20 nM FeEnt at 100 s (graph represents replicates combined from two separate experiments), and (C) is a graph showing the results of FM-labeled, frozen ΔfepA+pfepA-S278C thawed on ice and used in fluorescence spectroscopy assay using 10 nM FeEnt added at 100 s (graph represents replicates combined from two separate experiments);

FIG. 12 shows the adaptation of fluorescence assay to HTS format in *A. baumannii*, wherein (A) is a graph showing normalized fluorescence of *A. baumannii* ΔfepA+pfepA-S278C, (B) is a graph showing normalized fluorescence of *A. baumannii* ΔfepA+pfepA-T561C, and (C) is a graph showing Z' factors for each mutant control; and FIG. 13 is a series of images showing the results of FeEnt siderophore nutrition tests using lower concentrations of selected toxic compounds.

DETAILED DESCRIPTION

The present invention is concerned with a novel, cell-based high-throughput screening assay and screening techniques to investigate new compounds effective against Gram-negative bacteria, including antibiotic-resistant pathogens are described. The assay identifies compounds that inhibit bacterial iron transport, and more specifically identifies inhibitors of TonB-dependent FeEnt uptake by bacterial cells. It will be appreciated that inhibitor compounds may completely prevent transport of iron by the bacterial cells; however, a compound may also be considered an "inhibitor" if it hinders, restrains, or only partially prevents transport of iron by the cell.

In general, one aspect of the procedure involves site-directed labeling of specific amino acid residues on Gram-negative bacterial outer membrane proteins (i.e., iron transport proteins) with a detectable label (e.g., chemical label) or molecular reporter moiety. Exemplary detectable labels include fluorescent dyes or fluorophores. Once labeled, these sites become reporter groups (i.e., fluorescent probes) that convey information about the biochemical activities of the bacterial transporter proteins in the presence of iron. Hence the experimental system spectroscopically reports on when iron compounds bind to the protein, and when they are transported by the bacteria.

In one or more embodiments, the assay comprises contacting a candidate compound with a reaction solution in the presence of iron for a sufficient period of time, and detecting changes in the reaction solution over time. In one or more embodiments, the reaction solution comprises an engineered Gram-negative bacteria wherein the iron transport proteins on the bacterial outer membrane have amino acid residues that have been engineered with a detectable label (such as a fluorophore). In one or more embodiments, live bacteria with active iron transport capabilities are used in the reaction solution. The invention is suitable for use with any Gram-negative bacteria. In one or more embodiments, the engineered Gram-negative bacteria is selected from the group consisting of *Acinetobacter baumannii, Klebsiella pneumoniae, Pseudomonas aeruginosa, Enterobacter aerogenes*, and *Escherichia coli*.

An exemplary iron transport protein used in the invention is FepA. In one or more embodiments, the Gram-negative bacteria comprises a genetically-engineered or "mutated" FepA protein in the bacterial outer membrane. In one or more embodiments, the mutation comprises or consists of at least one amino acid residue of the native FepA protein substituted with a cysteine residue to generate the mutated FepA protein. In one or more embodiments, the cysteine substitution results in a "free cysteine" residue, which means that the location of the mutation results in the mutated cysteine residue being presented outwardly from the surface of the bacterial outer membrane, such that it is "free" to react for labeling. Accordingly, exemplary amino acid residues to be targeted for substitution should meet at least one, more preferably at least two, and preferably all three of the following criteria: (1) the targeted amino acid forms part of an outer loop of the FepA protein (so that the mutated cysteine residue will be outwardly presented); (2) the targeted amino acid position may vary, but is a conserved residue in FepA proteins across Gram-negative bacteria (as identified via sequence alignment with *E. coli* FepA); and (3) mutation of the targeted amino acid does not impair the native iron transport capabilities of the FepA protein. In general the targeted amino acid residues for mutation (and subsequent labeling) are those in the Fep A protein with small side chains that are localized on the cell surface. In one or more embodiments, the native amino acid residue to be substituted in the native FepA protein may be any amino acid, but is preferably selected from the group consisting of serine, glutamic acid, aspartic acid, alanine, and threonine. For example, when *E. coli* is the bacteria, suitable FepA residues targeted for cysteine substitution (and subsequent labeling) include residues 216, 271, or 398. Likewise, exemplary residues for substitution in *A. baumannii* include FepA residues 278, 561, or 664. It will be appreciated that the techniques illustrated in the working examples can be used to identify additional residues for substitution (and subsequent labeling) in other Gram-negative bacteria. Various known approaches can be used to engineer the bacteria to effect the cysteine substitution. Further, it will be appreciated that although wild type bacteria are preferred, the bacteria used in the invention may include other modifications in addition to the cysteine substitution described here, with the proviso that the native FepA iron transport capabilities of the bacteria are not impacted.

The engineered cells can then be labeled with a suitable fluorophore. In one or more embodiments, the cells are grown under iron-deficient conditions. In one or more embodiments, iron-deficient medium is used for culturing the engineered cells. The bacteria are then collected and suspended in phosphate buffer ($NaHPO_4$), with a pH of about 6.5-6.7, and preferably about 6.7. For labeling, the bacteria are then incubated with the selected fluorophore for a sufficient period of time, and under sufficient conditions to react with the free cysteine residue on the engineered bacteria. Preferably, the fluorophore is covalently attached to the engineered cysteine residue. In one or more embodiments, the fluorescent dye is a chemically-reactive derivative of fluorescein. For example, fluorescein maleimide is a sulfhydryl-reactive derivative of fluorescein that is preferred for use in the invention. In one or more embodiments, the fluorescein is incubated with the engineered bacteria in the phosphate buffer for at least about 5 min., and preferably from about 5 min. to about 25 min., and more preferably from about 5 min. to about 20 min. at a temperature of from about 0° C. to about 37° C., and a pH ranging from about 6.5 to about 6.7. The labeling reaction is then quenched, and the labeled cells are washed. The labeled cells are then suspended in an aqueous solution. Exemplary aqueous solutions include solutions that are non-toxic to the cells, and help maintain a neutral pH of the reaction solution in order not to destroy the cell and maintain the osmolarity of the cells. For example, buffer solutions including buffered saline solutions, such as phosphate buffered saline (PBS), are preferred aqueous solutions for used in the invention.

In one or more embodiments, the labeled cells are then used in the assay. In one or more embodiments, the labeled cells are suspended in a buffer solution along with a cryoprotectant, such as DMSO and/or glycerol, followed by cryopreservation of the labeled cells for future use. In one or more embodiments, the labeled cells can be cryopreserved for at least about 2 weeks before use in the assay.

For the assay, a candidate compound is incubated with the engineered and labeled bacteria in a reaction solution. Exemplary "candidate compounds" include any compound suspected of or having potential as an inhibitor of iron uptake, and more specifically TonB-dependent FeEnt uptake by the bacteria. Such compounds constitute new candidates for therapeutic applications against bacterial pathogens.

The reaction solution generally comprises the aqueous solution and at least one nutrient (i.e., carbon source) to support bacterial cell functioning in the reaction solution. Exemplary nutrients will depend upon the particular bacteria used, and include glucose, sodium acetate, succinate, and the like. The labeled cells are added to the reaction solution in a reaction vessel. In one or more embodiments, the reaction vessel is a microwell. In one or more embodiments, the microwell is part of a multi-well array in a microplate (aka microtiter plate). The plates may include 96, 384, or 1536, etc., wells disposed across the surface of the plate substrate, and generally arranged in a rectangular matrix. In general, the diameter, depth and spacing of the microwells in the plate can vary. In one or more embodiments, the reaction vessel has a working volume of 300 µL or less. It will be appreciated that the "working volume" of the reaction vessel is less than its total volume, and refers to the recommended volume to be utilized in individual vessels for the reaction solution, to avoid overflowing the vessel's total capacity. In one or more embodiments, the reaction vessel has a working volume of 75 µL or less. In one or more embodiments, the reaction vessel has a working volume of from about 25 µL to about 300 µL. Thus, the reaction solution volume in the inventive assay will comprise less than about 300 total solution, preferably from about 20 to about 300 and more preferably from about 25 to about 300 µL. It will be appreciated that an advantage of the inventive assays is miniaturization of the biochemical system to function in small volumes (≤300 µL), which allows the use of multi-compartment microtiter plates (e.g., 96- or 384-well plates). This adaptation of the methodology makes it compatible with high-throughput screening of chemical libraries to find inhibitors of bacterial iron uptake.

The cells density in the reaction solution in each reaction vessel may vary. In general low turbidity reaction solutions are desired. In other words, the cell density is preferably adjusted such that an adequate quantity of cells are present in each reaction vessel to generate a detectable signal; however, an excess concentration of cells in the reaction solution is counterproductive in that it causes adjacent cells to physically block the detectable signal from the reaction vessel. In one or more embodiments, cell density in the reaction solution ranges from about $5 \times 10^6$ to about $3 \times 10^7$ cells/ml, preferably from about $5 \times 10^6$ to about $2 \times 10^7$ cells/ml, and more preferably from about $5 \times 10^6$ to about $1 \times 10^7$ cells/ml. In one or more embodiments, the cell density is less than about $1 \times 10^7$ cells/ml. Optical density of the reaction solution can also be used to adjust the reaction solution cell concentration. Advantageously, the inventive methods can be used with cryopreserved bacterial cells. It will be appreciated that in the case of cryopreserved cells, the cells will be thawed and subjected to appropriate post-thawing protocols before use in the assay (e.g., centrifugation and washing to remove cryoprotectant).

The chemical compound of interest (aka candidate compound) is then added to the reaction solution in the reaction vessel. In one or more embodiments, a plurality of candidate compounds are assayed. For example, the reaction solution is distributed into a plurality of reaction vessels, such as a plurality of microwells in a microtiter plate. A plurality of candidate compounds are added to respective reaction vessels. In some cases, each reaction vessel contains a different candidate compound. In some cases, the same candidate compound can be added to a subgrouping of reaction vessels to provide an averaged result for that candidate compound across multiple reaction solutions. For example, one candidate compound can be added to a first quadrant of the array of microwells on a microtiter plate, while a second candidate compound can be added to a second quadrant of an array of microwells on a microtiter plate. In addition, it will be appreciated that different bacteria can be used in the reaction solutions across a multi-well plate. That is, a given microtiter plate does not necessarily have to assay the same bacteria in every microwell, but different bacteria may be present in respective microwells. Various combinations of types of bacteria and candidate compounds may be used, depending upon the desired design of the assay, as will be appreciated by those in art.

A source of iron is then added to the reaction solution. In one embodiment, FeEnt is added to the reaction solution, which is then incubated at room temperature (about 25° C.). In one embodiment, from about 5 to about 20 nM FeEnt (in PBS or water) is added to the reaction solution.

The assay is then monitored over time. More specifically, the detectable label on the FepA protein generates a signal that can be detected, and which changes over time depending upon the effect (or lack thereof) of the candidate compound on iron transport by the engineered bacteria. In general, the assay is observed or the plate is read before and after the addition of the iron source to the reaction solution, and after fluorescence recovery (transport of FeEnt). In particular, in the case of fluorescent labels, the assay solution is excited at the appropriate wavelength(s) and then observed for potential fluorescence quenching that occurs upon binding of iron (e.g., FeEnt), and then un-quenching (rebound) as the bacteria deplete it from solution by transport. For example, a first fluorescence reading is taken of the reaction solution before addition of the source of iron. A second fluorescence reading is then taken of the reaction solution immediately (i.e., about 1 second to about 120 seconds) after addition of the source of iron. A third fluorescence reading is then taken at least 5 minutes after addition of the source of iron, preferably from about 5 to about 45 minutes after addition of the source of iron, and more preferably from about 5 to about 30 minutes after addition of the source of iron. Various instruments are available for detecting the fluorescence signal, including commercially-available spectrophotometers.

In one or more embodiments, if the candidate compound is an inhibitor of iron transport, it will not necessarily affect iron binding, but will prevent transport. Accordingly, quenching of fluorescence is observed or detected in the assay at the second reading, but not un-quenching (recovery) at the third reading. In some cases, the candidate compound completely prevents iron transport. It will be appreciated that compounds that completely prevent TonB will permanently prevent fluorescence recovery, permitting flexibility in the timing of reading the assay (which can be delayed even hours after reaction). Some inhibitors may only partially inhibit iron transport, which is detectable based upon a decrease in the kinetics or intensity of the fluorescence rebound. By using live bacteria, the assay provides for real-time sequential quenching and un-quenching of fluorescence intensity that correlates with iron transport by the cells. This novel technique can be used to screen for candidate compounds with antimicrobial potential against any variety of gram-negative bacteria. Secondary screenings can also be carried out to verify the inhibitory potential of compounds identified by the novel assays, as described in detail in the working examples.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

A High-Throughput Screening (HTS) Assay for FeEnt Uptake in *Escherichia coli*

In this Example, a high-throughput screening (HTS) assay was created that detects FeEnt uptake through FepA in living *Escherichia coli*, by monitoring fluorescence quenching that occurs upon binding of FeEnt, and then un-quenching as the bacteria deplete it from solution by transport. The TonB-dependent Gram-negative bacterial outer membrane protein FepA actively transports the siderophore ferric enterobactin (FeEnt) into the periplasm, and is engineered for these assays to provide a detectable fluorescent signal for the assay. The assay can be used to identify inhibitors that block TonB function, and would constitute novel therapeutics against infectious disease caused by Gram-negative bacteria.

A. Materials & Methods

Bacterial Strains, Plasmids and Media.

*E. coli* strain OKN3 (ΔfepA), which carries a precise deletion of the fepA structural gene, was the host for derivatives of the low-copy plasmid pHSG575. The plasmid pITS23 carries the wild type *E. coli* fepA gene; pITS23FepAS271C is its derivative that encodes the substitution mutation S271C. All fepA genes were controlled by their native repressible Fur promoter. Cys residues were engineered into the FepA surface loops at position 271 (serine to cysteine substitution).

Instrumentation.

The fluorescent spectroscopic assays were conducted in an SLM/OLIS spectrofluorometer, that has an SLM 8000 chassis (Aminco, USA), upgraded to automatic control by an OLIS cpu, operating system and analysis software (OLIS Inc, Bogart, Ga.). For typical operations the excitation and emission wavelengths were 490 nm and 520 nm, respectively. The HTS assays were conducted on a Tecan GENios Pro (Tecan, Switzerland) with black round-bottom 96 well plates (Corning, USA). The excitation and emission filters were 485 nm and 535 nm, respectively.

Fluorescence Labeling.

After overnight growth in LB, OKN3/pITS23FepAS271C was subcultured under iron deficient conditions into 25 mL of MOPS minimal media (Neidhardt, F. C., Culture medium for Enterobacteria, J. Bacteriology, 119(3), 736-47 (1974)) with amino acids (at 100 ug/mL), streptomycin (50 μg/mL) and chloramphenicol (20 μg/mL), and shook the flasks 5.5-6 h at 37° C., until mid-log phase (~$5\times10^8$ cells/mL). Cells were collected by centrifugation at 8000×g for 10 min, followed by resuspension of the pellets in 10 mL of 50 mM $NaHPO_4$, pH 6.5-6.7. The cells were re-pelleted by centrifugation and resuspended in 10 mL of the same phosphate buffer ($NaHPO_4$) at pH 6.5-6.7. The bacteria were then exposed to 5 μM fluorescein maleimide (FM) for 5-20 min at 37° C. The labeling reaction was quenched with 1 mM 2-mercaptoethanol, and the labeled cells were collected by centrifugation, washed and resuspended in phosphate buffered saline (PBS). The cell concentrations were adjusted based upon their optical density at 600 nm.

FeEnt Quenching and Uptake.

When FeEnt binds to the fluoresceinated FepAS271C in living *E. coli*, fluorescence is quenched. As the bacteria transport the iron complex and deplete it from solution the fluorescence signal rebounds. Because OM transport of FeEnt is TonB-dependent, this assay can be used to identify inhibitors of TonB action that block iron uptake, and thereby prevent fluorescence recovery. *E. coli* OKN3/pITS23FepAS271C-FM, stored on ice, was warmed to 37° C. for 30 min in PBS plus 0.4% glucose in the absence or presence of inhibitors (see below), then diluted to $2.5\times10^7$ cells/mL in 2 mL of the same buffer in a 3 mL quartz cuvette with stirring in the SLM/OLIS spectrofluorometer. Initial readings of fluorescence intensity were recorded. Next, FeEnt was added to the solution to the indicated final concentration, and changes in fluorescence emissions during its binding and transport were monitored and recorded. The data was normalized to account for variations in labeling efficacy, cell number, etc., and results were analyzed with GraFit 6.011 (Erithacus Ltd, Middlesex, UK).

Inhibitors.

To observe the effects of metabolic inhibitors (carbonyl cyanide m-chlorophenylhydrazone (CCCP), 2,4-dinitrophenol (DNP), azide, cyanide and arsenate) in the assay, fluoresceinated cells were pre-incubated for 30 minutes at 37° C. with serial dilutions of different compounds in PBS plus 0.4% glucose, prior to initiation of the assay. The inhibitor was included at the same concentration in the cuvette or microplate. Bacterial cell concentrations, addition of FeEnt, sample mixing, fluorescence measurements and data analysis were the same as above. Based on data collected in the presence of sequential concentrations of the inhibitors (5-point dose-response curves), 50% inhibitory values represent the final concentration of the test compound that allowed 50% recovery of fluorescence during the uptake time course; at the 100% inhibition level, no fluorescence recovery was observed.

Cell and FeEnt Concentrations in Microtiter Plates.

The rate of depletion of extracellular FeEnt, and consequently the rate of the fluorescence response was related to the concentrations of cells and FeEnt in the microplate wells. The reaction was observed over a range of cell densities and FeEnt concentrations in a Tecan GENois fluorescence microplate reader. Labeled cells were added to a 96 well plate at decreasing densities ($2.5$-$0.07\times10^7$ cells/mL), in a total well volume of 190 μL of PBS plus 0.4% glucose. After measuring unquenched fluorescence by readings with 485 nm and 535 nm excitation and emission filters, respectively, FeEnt (10 uL) was added to a final concentration of 200 nM in all of the wells with automatic injectors. The high concentration of FeEnt ensured maximal quenching across all cell densities. It will be appreciated that [FeEnt] is an adjustable parameter that can vary with cell concentration to achieve different extents and durations of quenching. After shaking the plate for 10 seconds the FeEnt transport time course over 110 minutes was measured by plate readings at 10 min intervals (each read cycle was completed within ~1 min), and averaged triplicate measurements were analyzed with GraFit 6.011.

Z' Factor.

Z-factor calculations estimated the statistical significance of the HTS results and the viability of assay. Positive and negative controls were used in the calculations to determine the statistical effect size.

B. Results

Fluorescence Spectroscopic Measurement of TonB-Dependent Transport.

*E. coli* FepA can be FM-labeled in its surface loops, and loop closure around FeEnt during binding quenches emissions from the probe. When fluoresceinated bacteria transport FeEnt, it becomes depleted from solution and fluorescence rebounds (FIG. 1A). Control experiments in energy- and TonB-deficient bacteria confirmed the interpretation of these observations. Thus transport appears as real-time quenching and un-quenching of fluorescence intensity, and the extent and duration of quenching depends on the concentrations of bacteria and FeEnt in the cuvette, the temperature and the incubation time. Variation of these parameters allowed modification of the assay to encompass a spectrum of read times and the inclusion of potential inhibitors.

The primary obstacle to accurate measurements with this spectroscopic test is light absorption/scatter by the bacterial cells, which may obscure light emissions by the extrinsic fluorophore. In practice, dilute bacterial suspensions (i.e., low turbidity) produced the best usable data. The assay therefore required high-intensity, specific labeling of FepA, that allowed utilization of dilute cell solutions (i.e., less than $2.5 \times 10^7$ cells/ml) without loss of the fluorescence signal. The protocol utilized conditions that maximize specific labeling of the engineered Cys residues in FepA surface loops: 5 uM FM in 50 mM $NaHPO_4$, pH 6.5, 5 min. at 37° C.

To observe the dose-response behavior of FeEnt in the fluorescence assay of iron transport through FepA a range of concentrations (1, 2, 4, 8, 16, and 32 nM) of the ferric siderophore (FIG. 1B) were tested in the SLM/OLIS fluorometer. The extent of quenching directly related to the concentration of FeEnt added, up to 16 nM; both 16 nM and 32 nM caused maximum fluorescence quenching. The rate of depletion of extracellular FeEnt was inversely proportional to the amount of FeEnt added; fluorescence recovery occurred within a few minutes for all samples except those exposed to 16 nM and 32 nM FeEnt (that did not un-quench over 8 minutes).

The SLM/OLIS fluorescence platform established a framework for similar studies in the microtiter format of a Tecan GENios plate reader. Instead of continuous measurements of dynamic fluorescence as seen in the SLM/OLIS, an assay was designed that involved 3 fluorescence reads (FIG. 1A) to allow evaluation of FeEnt uptake, and its inhibition, in a high-throughput format. The three measurement points (marked in FIG. 1A with black rectangles) occur before addition of FeEnt, after addition of FeEnt, and after incubation that allowed transport of FeEnt. The third read time is flexible and may occur any time after fluorescence recovery. Three time courses (FIG. 1A) illustrated the assay concept: addition of PBS, or FeEnt, or FeEnt plus an energy poison (DNP) to the cells. The inhibitor did not affect binding but prevented transport, thereby allowing quenching of fluorescence but not un-quenching (recovery). The assay acted like a molecular light switch that was turned on by TonB activity and off in its absence.

Fluorescence Measurements in Microtiter Format.

The assay was miniaturized for HTS in the Tecan Genios fluorometer by adjusting the [FeEnt], the number of cells in the wells, and the transport time. A 190 uL suspension of OKN3/pITS23FepAS271C-FM in PBS and 0.4% glucose were added to the microtiter plate microwells, along with the potential inhibitor compounds. The starting fluorescence was measured at 535 nm. Next, 10 uL FeEnt was added by automatic injection and its uptake time course was monitored. The basic process involved 3 emission readings at 535 nm: a $1^{st}$ reading of fluoresceinated bacteria alone (in the absence or presence of inhibitors); a $2^{nd}$ reading following automated injection of 5 nM FeEnt; a $3^{rd}$ reading after incubation for 30 min at RT to allow FeEnt uptake. With bacterial cells at ~$10^7$ cells/mL we saw transport of 5 nM FeEnt as the expected quenching and recovery of fluorescence intensity in the 96 well plates. Thus, the test correctly functioned in a 200 uL total volume space, creating a high-throughput platform for identification of compounds that block TonB-dependent FeEnt uptake.

Relative to the SLM/OLIS instrumentation the high-throughput Tecan instrumentation allowed simultaneous testing of more methodologies and samples in 96- or 384-well black plates. The preferred cell concentration for HTS was determined by evaluating a decreasing range of cell densities from $2.5$-$0.07 \times 10^7$ cells/mL (FIG. 1C). When FeEnt was added to the wells at 200 nM the fluorescence of all samples was quenched, indicating that cell density determined the rate of fluorescence rebound. At $2.5 \times 10^7$ cells/mL fluorescence recovered within 40 minutes, while a 10-fold dilution of the bacteria delayed recovery for an additional hour. Signal intensity also proportionally decreased with the concentration of the fluoresceinated bacterial cells, from 40 at $2.5 \times 10^7$ cells/mL to 5 at $0.19 \times 10^7$ cells/mL. However, even in the latter dilute suspensions, FeEnt transport was apparent as quenching/unquenching in sequential plate reads.

Bacterial Viability, Reproducibility and Optimization of Cell and FeEnt Concentration.

Figure 2:
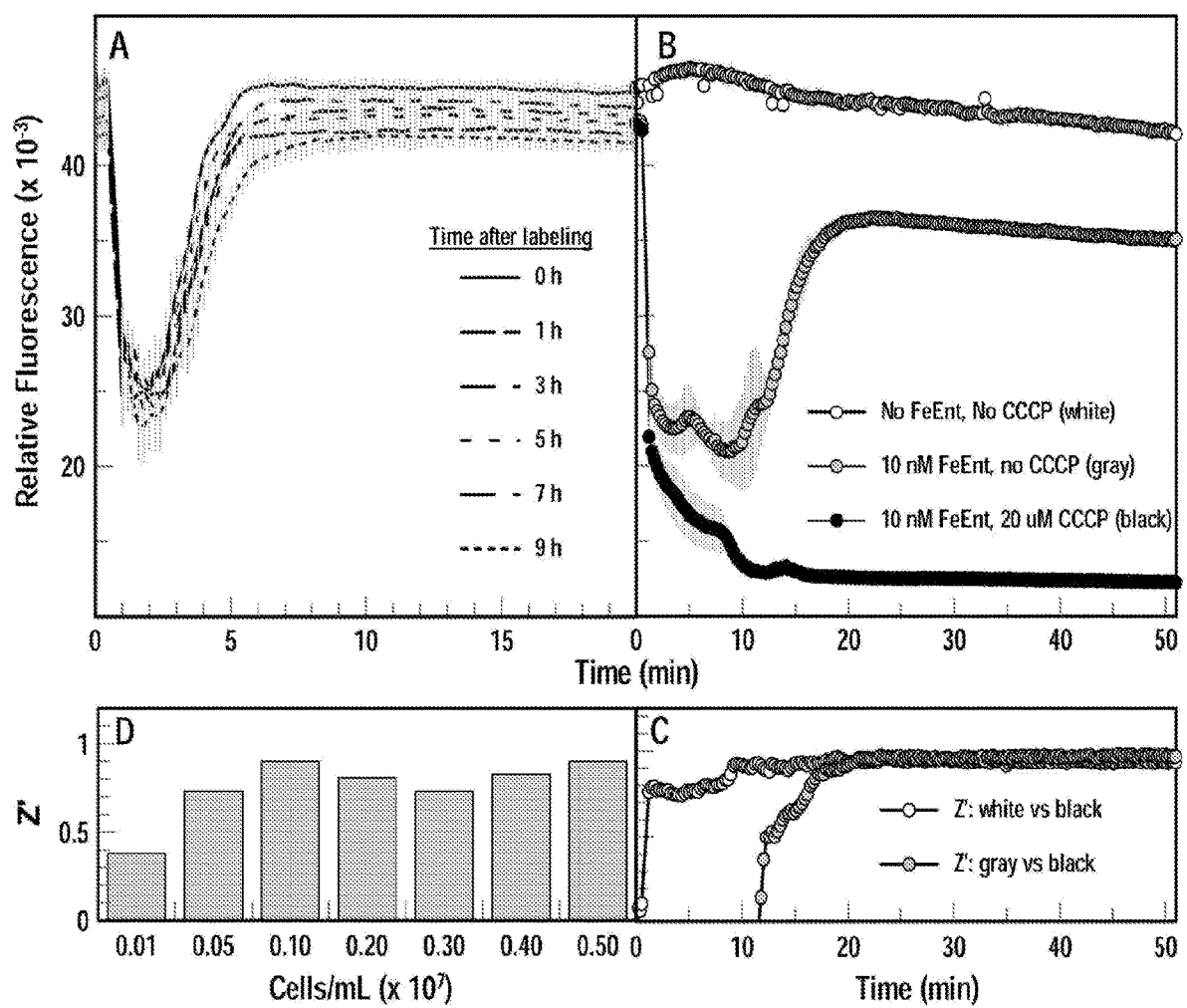

High-throughput screening often lasts hours, so the ability of fluoresceinated bacteria to transport FeEnt after storage in the cold was evaluated. Cells were engineered and labeled as described and stored on ice for 0, 1, 3, 5, and 9 h. Next, aliquots were reconstituted in PBS plus 0.4% glucose to $10^7$ cells/mL in microplates at room temperature. After measuring unquenched fluorescence, FeEnt was dispensed into the microwells with automatic injectors to a final concentration of 20 nM. The plates were agitated for 10 seconds, and the FeEnt transport time course was observed over 95 cycles. The results showed the resilience of the bacterial cells, with <10% decay in cellular fluorescence (probably from cell lysis) over the 9 h at 0° C., and otherwise no noticeable effect on FeEnt uptake. FeEnt quenched all samples to ~40% of original fluorescence intensity, and little variation occurred in the speed of fluorescence recovery: all test samples regained their original intensity within 8 minutes (FIG. 2A).

Even after extended storage on ice for 11 h, FeEnt uptake by the fluoresceinated cells in microwells recapitulated the concentration-dependence of quenching/un-quenching (FIG. 2B) as previously seen for freshly grown and labeled bacteria (FIG. 1C). Furthermore, Z factor calculations from the stored cells were acceptable and amenable to HTS. FeEnt (to 10 nM) was added by automatic injection to cells in microplates, agitated for 10 s, and measured the transport time course. For each condition (no additions, or plus FeEnt (10 nM), or plus FeEnt (10 nM) and CCCP (20 uM)) fluorescence was followed in three separate wells of a 96-well plate, sequential plate reads were made over 50 minutes, and triplicate values were averaged (FIG. 2B). The statistical significance as determined by Z factors (FIG. 2C) validated this extended protocol, which allowed storage of fluoresceinated bacteria overnight on ice prior to use in the assay. Lastly, cell density was an influential parameter of the HTS procedure. For bacterial concentrations from $5\times10^6$/mL-$5\times10^7$/mL, Z factors were found in the range 0.7-0.9 (FIG. 2D). These results demonstrate the resilience of the cells and reproducibility of the measurements in an HTS microplate format. Some day-to-day variability occurred from one batch of labeled cells to another, but quenching and recovery were as consistent in microplates as in cuvettes.

Effects of Inhibitors.

The effects of metabolic inhibitors were initially studied in the SLM/OLIS fluorometer, which revealed the following order of sensitivity: CCCP>DNP>cyanide>azide>arsenate. Pre-incubation of the bacteria with 0.005 mM CCCP reduced the extent of fluorescence recovery 50% ($IC_{50}$), and 0.01 mM CCCP prevented any recovery ($IC_{100}$). We determined $IC_{50}$ and $IC_{100}$ for each of these compounds (Table 1). Proton ionophores (CCCP, DNP), electron transport inhibitors (cyanide, azide), and even the phosphate analog arsenate blocked active iron transport.

TABLE 1

Inhibitory concentrations of energy poisons

| Compound | Concentration (mM) | |
| --- | --- | --- |
|  | 50% Inhibition | 100% Inhibition |
| CCCP* | 0.005 | 0.01 |
| DNP | 0.75 | 1.5 |
| Cyanide* | 2-3 | 9 |
| Azide | 9 | 18 |
| Arsenate | 90 | 180 |

50% inhibitory values represent the final concentration of the test compound that allowed 50% recovery of fluorescence during the uptake time course; at the 100% inhibition level, recovery of fluorescence was not observed.

The microtiter fluorescence assay recapitulated the inhibitory effects of CCCP on TonB-dependent FeEnt uptake (FIG. 2B). The fluorescence of the unaltered bacterial cells was stable over the 50 min time course with minimal variation; FeEnt binding by FepAS271C-FM quenched fluorescence, its depletion from solution by transport un-quenched fluorescence, and the inclusion of CCCP (20 uM) fully prevented fluorescence recovery. The high Z-factors calculated from these samples at the third time point validate the fluorescence HTS approach to identification of inhibitors of FeEnt uptake: compounds that blocked TonB-dependent transport (in this case an energy poison) had Z factors of ~1.0 any time after 20 minutes (FIG. 2C).

Example 2

HTS Assay for FeEnt Uptake in Gram Negative Bacteria

In this Example, additional investigation was carried out with E. coli to continue the work described in Example 1 above. Further, the approach was validated in an additional Gram-negative bacteria, A. baumannii, to demonstrate the applicability of the assay to screening for inhibitors of TonB-dependent FeEnt transport in any Gram-negative bacteria.

A. Materials and Methods

Bacterial Strains and Reagents.

All experiments with E. coli were performed using MG1655 or BN1071 and its derivatives OKN1 (ΔtonB ΔfepA), OKN7 (ΔtonB), OKN3 (ΔfepA), OKN3+pITS23 (ΔfepA+pfepA), and OKN3+pITS23-S271C as described in Example 1 above. All experiments with Acinetobacter baumannii were performed with A. baumannii ATCC 17978 (incorporated by reference herein) or a mutant derivative (ΔfepA) generated herein. Strains were cultured in Luria broth (LB) at 37° C. with aeration and $OD_{600}$ used to measure bacterial growth unless otherwise noted. Selection on ampicillin (Sigma) was 100 µg/mL for E. coli and 500 µg/mL for A. baumannii. Selection on streptomycin (Sigma) was 100 µg/mL and chloramphenicol (Sigma) was 20 µg/mL. MOPS minimal media was used as described above. Carbonyl cyanide-m-chlorophenylhydrazone (CCCP) powder (Sigma) was prepared as 10 mM stock in DMSO (Alfa Aesar, Haverhill, Mass.) and stored at −20° C. For secondary screening, compounds were obtained as fresh solids by suppliers and suspended to 10 mM in DMSO and stored at −20° C. until use.

Generation of Deletion Mutants and Complementation Vectors.

E. coli deletion and complementation strains are described above. For generation of A. baumannii ΔfepA, approximately 1000 base pairs of DNA in both the 5' and 3' flanking regions surrounding each open reading frame were amplified from A. baumannii genomic DNA. Subsequently, the pFLP2 suicide vector was amplified. The three PCR products were stitched together using the method of Gibson et al. (Enzymatic assembly of DNA molecules up to several hundred kilobases. Nature methods 6, 343-345, (2009)), with the NEBuilder HiFi cloning kit (New England Biolabs), and the construct was sequence verified. This vector was then transformed into A. baumannii by electroporation, and bacterial integrants were selected for on LB Amp500 agar grown overnight at 37° C. Transformants were patched onto LB Amp500 or LB with 10% sucrose, and merodiploids were Amp$^R$ sucrose$^S$. To resolve the integrated plasmid, merodiploid strains were grown overnight in 3 mL LB and incubated overnight at 37° C. with shaking. Cultures were serially diluted, plated on LB agar with 10% sucrose, and incubated overnight at 37° C. Transformants were patched on LB Amp500 and LB agar and incubated at 37° C. overnight. The Amp$^S$ strains were screened for the loss of fepA by multiple PCR reactions.

For fepA complementation in A. baumannii, the native promoter, fepA gene, and terminator and also the fepA gene alone were amplified from A. baumannii genomic DNA incorporating BamHI and SalI restriction sites at the 5' and 3' ends, respectively. Following digestion, these two constructs were ligated into pWH1266 or p2682pro (Nairn et al., 2016) to make pfepA and p2682profepA, respectively. For each vector, the integrity of the promoter, terminator, and gene were confirmed by sequencing (McLab, San Francisco, Calif.). The empty vector and the complementation vectors were each transformed into the respective deletion mutant by electroporation. In addition, the empty vector was transformed into wild-type A. baumannii in order to account for any potential growth differences associated with the vector.

Fluorescence Labeling and Spectroscopy.

For covalent modification of cysteine residues in live cells, after overnight growth in LB broth, the *A. baumannii* was sub-cultured in Nutrient broth and *E. coli* in MOPS minimal media plus Sm100 Cm20. All cultures were shaken at 37° C. until they reached $OD_{600}$=1.0-1.5. Cells were collected by centrifugation, washed with 50 mM $NaHPO_4$, pH 6.7 and then suspended in the same buffer. FM was prepared by dissolution in DMSO; its concentration was spectrophotometrically determined ($\in$493 nm=81,500 $M^{-1}$) after dilution into 10 mM Tris-Cl, pH 8.0. FM was added to bacterial cultures at 5 µM, and incubated for 20 min at 37° C. in the dark. Reaction was quenched with 1:100 dilution of 130 mM β-mercaptoethanol and then cells were pelleted, washed in 1×PBS+50 mM sodium acetate for *A. baumannii* or 1×PBS+0.4% glucose for *E. coli*, and suspended in the same buffer.

Spectroscopic assays were performed in an SLM/OLIS spectrofluorometer that has an SLM 8000 chassis (Aminco, Lake Forest, Calif.), upgraded to automatic control by an OLIS cpu, operating system, and analysis software (OLIS, Inc., Bogart, Ga.). The excitation and emission wavelengths were 490 and 520 nm, respectively. Labeled cells were diluted to $2.5 \times 10^7$ cells/mL in 2 mL of the same buffer in a 3 mL quartz cuvette. We collected initial readings of fluorescence intensity, added FeEnt to the indicated final concentration, and monitored changes in fluorescence emissions during its binding and transport.

For microtiter format, the Tecan GENios microplate reader (Tecan, Switzerland) was used. Frozen or fresh labeled cells were added to black, round bottom 96-well (Corning, Lowell, Mass.) or 384-well (Greiner Bio-One, Monroe, N.C.) plates to a 190 µL or 95 µL total volume, respectively, of 1×PBS+0.4% glucose or 50 mM acetate as for SLM. After three reads of initial fluorescence reading at 485 and 535 nm excitation and emission filters, respectively, FeEnt was added at the designated concentration to each well using the automatic injector. After shaking the plate for 10 s, transport was evaluated over a time course with reads every minute. Freshly labeled cells were also frozen at −80° C. in 20% glycerol and frozen cells were thawed on ice and warmed to 37° C. prior to evaluation of transport in either format of the fluorescence assay. Cells were viable and able to transport FeEnt with similar kinetics following freezing for at least 1 month by this method. For all fluorescence assays, raw fluorescence volt values were normalized to account for variations in labeling efficacy and cell number and represented as fluorescence (F) over initial fluorescence (F0). Z factors were calculated for the positive and negative controls in order to determine the statistical effect size and using the following equation: $Z'=1-(3*\sigma_{+c}+\sigma_{-c})/(|\mu_{-c}-\mu_{+c}|)$. The raw and normalized values were plotted using GraFit 6.011.

Primary HTS Assay.

*E. coli* OKN3+pITS23-S271C was grown and labeled with FM as described in Example 1 above, and labeling and transport were confirmed by spectroscopic assay above. Cells were then aliquoted at $2 \times 10^8$ cells/mL, frozen at −80° C. for 1 h, and transported to University of Kansas HTS facility on dry ice. Assay was validated on the frozen cells plus or minus CCCP controls in the BioTek Synergy microplate reader (BioTek, Winooski, Vt.) prior to performing the HTS screen. Four libraries totaling 17,441 compounds were assayed in 384-well plate format using $2 \times 10^7$ cells in PBS+0.4% glucose. Fluorescence was assayed in the BioTek Synergy (Gain=90, excitation=495 nm and emission=520 nm) at three time points, F1=initial fluorescence after 1 min, F2=1 min after addition of FeEnt, and F3=60-80 min following addition of FeEnt and incubation at 37° C. Bacteria+FeEnt+100 µM CCCP and bacteria+FeEnt+DMSO were included as controls on each plate.

Data Analysis and Dose-Response on Primary Hits.

Z' scores were determined for each plate, and a scattergram of all compounds was plotted to determine the median and standard deviation (SD). Any compounds that fell equal to or greater than a SD=2.0 (165 compounds, Table 2) were selected for dose-response curves.

TABLE 2

| Library | Total # compounds | Selections* | >30% Inhibition | 20-30% Inhibition | <20% Inhibition | Hit Rate (overall) |
|---|---|---|---|---|---|---|
| CMLD | 5208 | 61 | 4 | 30 | 27 | 0.19 |
| TimTec Actiprobe 5K | 5000 | 39 | 9 | 9 | 21 | 0.10 |
| FDA/ Bioactives | 5233 | 37 | 15 | 6 | 16 | 0.12 |
| Microsource Spectrum | 2000 | 28 | 16 | 5 | 7 | 0.12 |
|  | 17441 | 165 | 44 | 50 | 71 | 0.54 |

*Compounds were cherry-picked by selection of any compounds whose % inhibition at read 3 was ≥2 S.D. from the median (15% cut-off). Hit rate represents # of compounds >20% inhibition out of total # of compounds.

Each compound was tested at 0, 2.5, 5 10, and 20 µM in the fluorescence assay described above but in a kinetic format, with fluorescence reads every min for 80 min. Compounds were then categorized by percent inhibition: >30% inhibition, 20-30% inhibition, and <20% inhibition. The 44 compounds with >30% inhibition were considered hits. Of those, any compound that only affected the recovery phase (not initial fluorescence or quenching) were followed up with secondary screening assays.

Siderophore Nutrition Test.

*A. baumannii* or *E. coli* were grown overnight in LB and then re-seeded 1:100 into Nutrient broth with antibiotics as appropriate and grown for 5.5 h at 37° C. with shaking. From these cultures, 100 µL were added to NB top agar containing 100 µM apoferrichrome A (Wayne et al., 1976) in 6-well plates. Sterile, filter paper disks (6 mm diameter) containing 10 µL of 50 µM FeEnt or Fc were applied to the plates and then incubated at 37° C. for 24 h. Siderophore utilization was represented by bacterial growth surrounding the disc. For secondary screening with compounds, each compound was added to bacteria and top agar prior to adding siderophore containing discs at a 100 µM concentration. CCCP control was added at 15 µM concentration and DMSO control was included using a range of volumes to ensure no toxicity as a result of the DMSO.

Colicin Killing Assay.

The titer of each colicin was tested by spotting a titration of colicin on a lawn of cells on LB agar. Titer was determined by the reciprocal of the last dilution which gave discernable killing of the cells. For evaluating the impact of each compound to colicin killing, cultures of MG1655 were cultured overnight in 5 mL LB as required. Overnight cultures were back-diluted 1:100 in 5 mL of MOPS as required for 6 h, at which point bacteria were normalized to a concentration of $1\times10^4$ CFU/mL as determined by $OD_{600}$ and confirmed by serial dilution and plating on agar. For each strain, 100 μL of cells plus sub-toxic concentration of compound (as determined by MIC assay) was incubated for 15 min at 37° C. Colicin was diluted to the previously determined lowest toxic titer and added directly into 100 μL cells plus inhibitor. For each compound, plates with no treatment, colicin only, or compound only controls were included. This mixture was incubated for 15 min at 37° C. and then spread onto LB agar plate surface and incubated at 37° C. After 16 h, colony numbers were determined for each plate. The number of hits per cell in the presence or absence of inhibitor is determined by the equation $S/S_0 = e^{-k}$, where S is the number of colonies in the presence of colicin (cells that survive colicin exposure), $S_0$ is the number of colonies in the absence of colicin, and k is the number of hits per cell. These numbers were used to quantitatively compare colicin killing between compounds. Each compound was tested in at least three separate experiments and an average of three replicates was represented as % killing or % survival using GraFit 6.011.

Minimal Inhibitory Concentration Assay.

E. coli MG1655 was cultured overnight in LB and then diluted 1:100 into LB plus or minus compound. Each compound was tested at a range of concentrations in a two-fold dilution series from 0.25-512 μM. The minimal inhibitory concentration was determined as the minimal concentration of compound that resulted in no growth, and any compound that did not prevent growth at 512 μM was considered non-inhibitory. Untreated MG1655 and MG1655 treated with the corresponding volumes of DMSO were included as controls, and each compound was tested in 2-3 separate experiments.

Growth Assay in Iron-Limiting Conditions.

WT A. baumannii and ΔfepA A. baumannii were grown overnight in LB, then back-diluted 1:100 into MOPS minimal media plus or minus 100 μM apoFcA and evaluated for growth over an 8 h time course. For evaluation of growth using FeEnt as an iron source, strains were grown overnight in LB, then back-diluted into MOPS minimal media+100 μM apoFcA, and then further diluted 1:100 into MOPS minimal media plus or minus 1 μM FeEnt and evaluated for growth over an 8 h time course.

FeEnt Accumulation Assay.

Accumulation of FeEnt was measured using $^{59}$FeEnt. $^{59}$FeEnt was prepared at a specific activity of <200 c.p.m. $pM^{-1}$ and chromatographically purified. Bacteria were grown for 5.5 h in MOPS minimal media plus 50 mM sodium acetate at 37° C. with shaking and then 2 cultures maintained at 37° C. for the duration of the assay. Pre-warmed MOPS minimal media plus 50 mM sodium acetate containing 1 μM $^{59}$FeEnt was poured into the tube. After 5, 15, 30, and 45 min incubating at 37° C., the cultures were filtered through 0.45 mm nitrocellulose, and transport quenched with 10 mL 0.9% LiCl. The filters were counted in a Cobra Quantum gamma counter (Perkin Elmer, Inc., Waltham, Mass.). An average of replicate experiments was plotted using the enzyme kinetics equation in GraFit 6.011.

FeEnt Transport Assays.

For A. baumannii, FeEnt transport was assayed using $^{59}$FeEnt. Bacteria were grown for 5.5 h in MOPS minimal media plus 50 mM sodium acetate at 37° C. with shaking and then deposited in a 50 ml test tube and incubated in a 37° C. water bath. Without delay, 10 ml of pre-warmed MOPS minimal media plus 20 mM sodium acetate containing varying concentrations of $^{59}$FeEnt was poured into the tube. After 5 seconds or 1 min, the cultures were immediately filtered through 0.45 mm nitrocellulose, and transport quenched with 10 mL 0.9% LiCl. The filters were counted in the Cobra Quantum gamma counter. Kinetic parameters were determined from the initial rates of FeEnt uptake, which were calculated at each substrate concentration from two independent measurements made in triplicate at 5 s and 1 min: c.p.m. bound to the cells at 5 s were subtracted from the c.p.m. associated with the cells at 1 min. An average of replicate experiments was plotted using the enzyme kinetics equation in GraFit 6.011, which also provided $K_m$ and $V_{max}$ calculations.

Site-Directed Mutagenesis for Cysteine Substitution of FepA.

Structural modeling for AbaFepA was performed using the UCSF Chimera program. The amino acid sequence was threaded against the crystal structure of EcoFepA to generate a model of the structure of AbaFepA. From this model, several residues were chosen in different predicted exposed loops based on previously-successful amino acids used to modify EcoFepA for FM labeling.

Mutations were engineered on pfepA using QuikChange II XL mutagenesis kit (Agilent, Santa Clara, Calif.). Specifically, using pfepA as a template, site-directed cysteine substitution mutations in AbaFepA were generated for T222, S278, A325, T382, T481, T561, S664, and S711. After verification by DNA sequence analysis, each construct was transformed into ΔfepA and FeEnt transport of each strain was evaluated via FeEnt nutrition test to ensure expression equivalent to the pfepA complementation strain.

B. Results

High-Throughput Screening Via Fluorescence Spectroscopy Monitoring TonB-Dependent Transport of FeEnt by FepA in E. coli.

Figure 3:
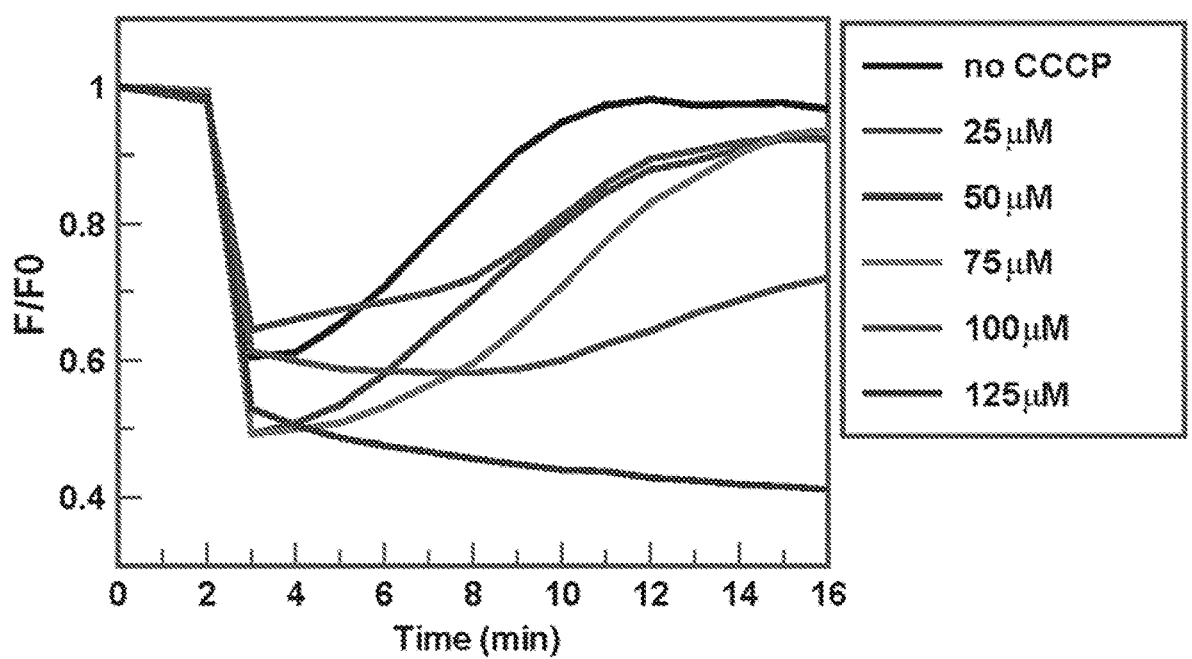

Considering the crucial role TonB plays in the transport of siderophores and other molecules important to Gram-negative bacteria, we sought to identify small molecule inhibitors of TonB-dependent transport via an HTS approach. We have previously developed a fluorescence-based assay to specifically monitor to transport of FeEnt by FepA in live E. coli cells using a 96-well microtiter plate format in Example 1. In order to perform the HTS, the fluorescence assay was first adapted to 384-well microtiter plate format. The fluorescence assay in the 384-well plate format displayed similar kinetics to the SLM and 96-well plate versions of the assay (FIG. 3). Specifically, labeled bacteria showed dose-responsive decrease in recovered fluorescence with increasing concentrations of the PMF-inhibitor CCCP but not the DMSO control. Importantly, labeled, frozen cells of up to 2 weeks were viable and able to transport FeEnt as detected by the fluorescence assay; complete recovery took 10-15 min in the microtiter format (FIG. 3). The ability to freeze labeled cells for subsequent use in the fluorescence assay enables the performance of a multi-day HTS. Together, these data demonstrated that the fluorescence assay is suitable for HTS.

Figure 4:
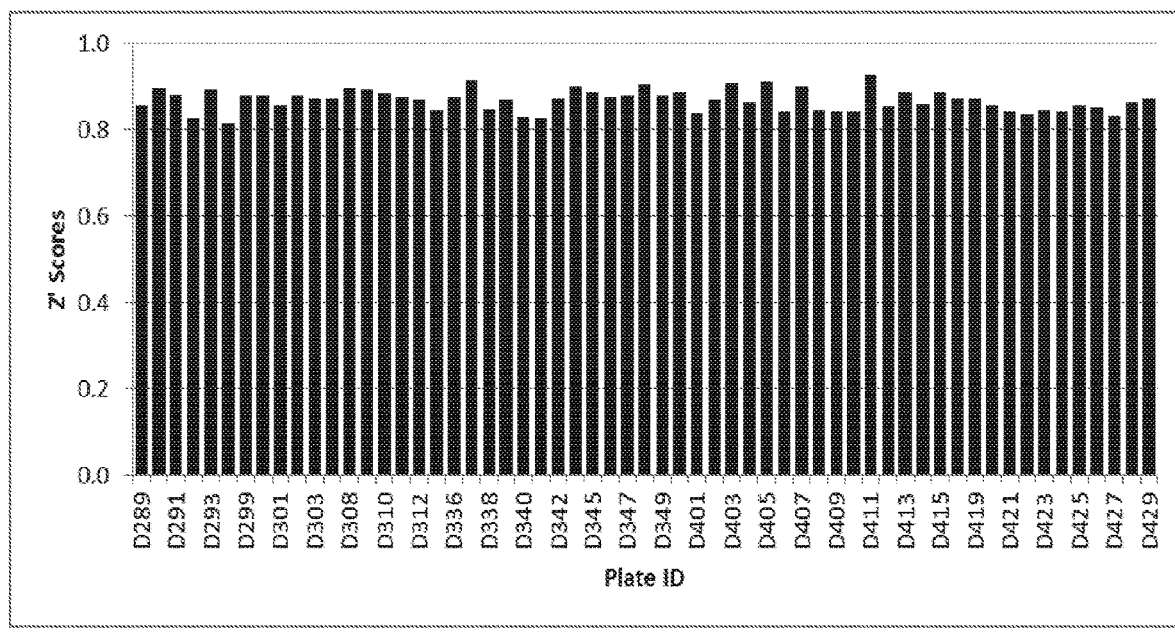
Figure 4:
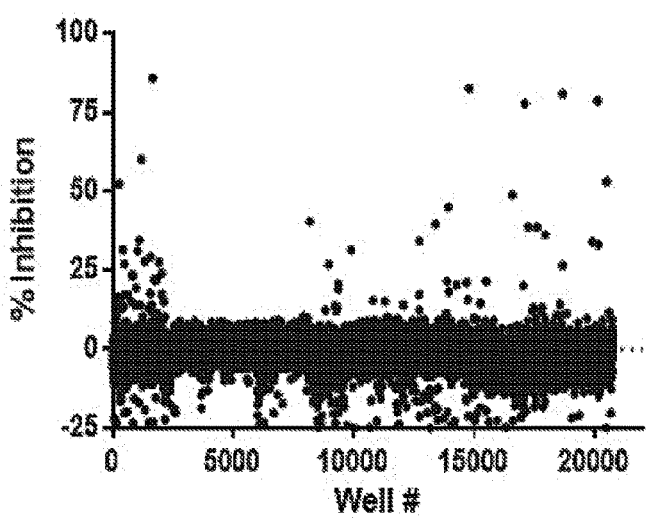

The high-throughput screen was performed using four chemical libraries totaling 17,441 compounds: Microsource Library (2000 compounds, 10 FDA/Bioactives (5233 compounds, 5 University of Kansas Center of Excellence in Chemical Methodologies & Library Development (KU CMLD) Library (5000 compounds, 10 and TimTec Actiprobe 5K (5000 compounds, 10 µM) (Table 2). Each plate included the following controls: no bacteria (16 wells), bacteria with CCCP (8 wells), and bacteria with no CCCP (8 wells, untreated). For fluorescence quenching and transport, 10 nM FeEnt was added to all wells. For evaluation of transport and inhibition of transport by compounds, two fluorescence reads were measured, first the initial fluorescence (1 min) and the final fluorescence (60-80 min). The overall Z' factor was 0.87±0.02 when compared across all plates (FIG. 4A). The 165 compounds that inhibited at greater than 2 standard deviations from the median (FIG. 4B) were selected for primary screen validation via dose-response assays using 0, 2.5, 5, 10, and 20 µM of each compound and measured kinetically for 80 min following addition of 10 nM FeEnt. From these data, the compounds were placed into three categories: <20% inhibition, 20-30% inhibition, and >30% inhibition. All compounds with >20% inhibition were considered true hits, resulting in an overall hit rate of 0.54%. Overall, the primary screen yielded a reasonable number of hits to follow up with secondary screens.

Secondary Screening of Primary Screen Hits.

Figure 5:
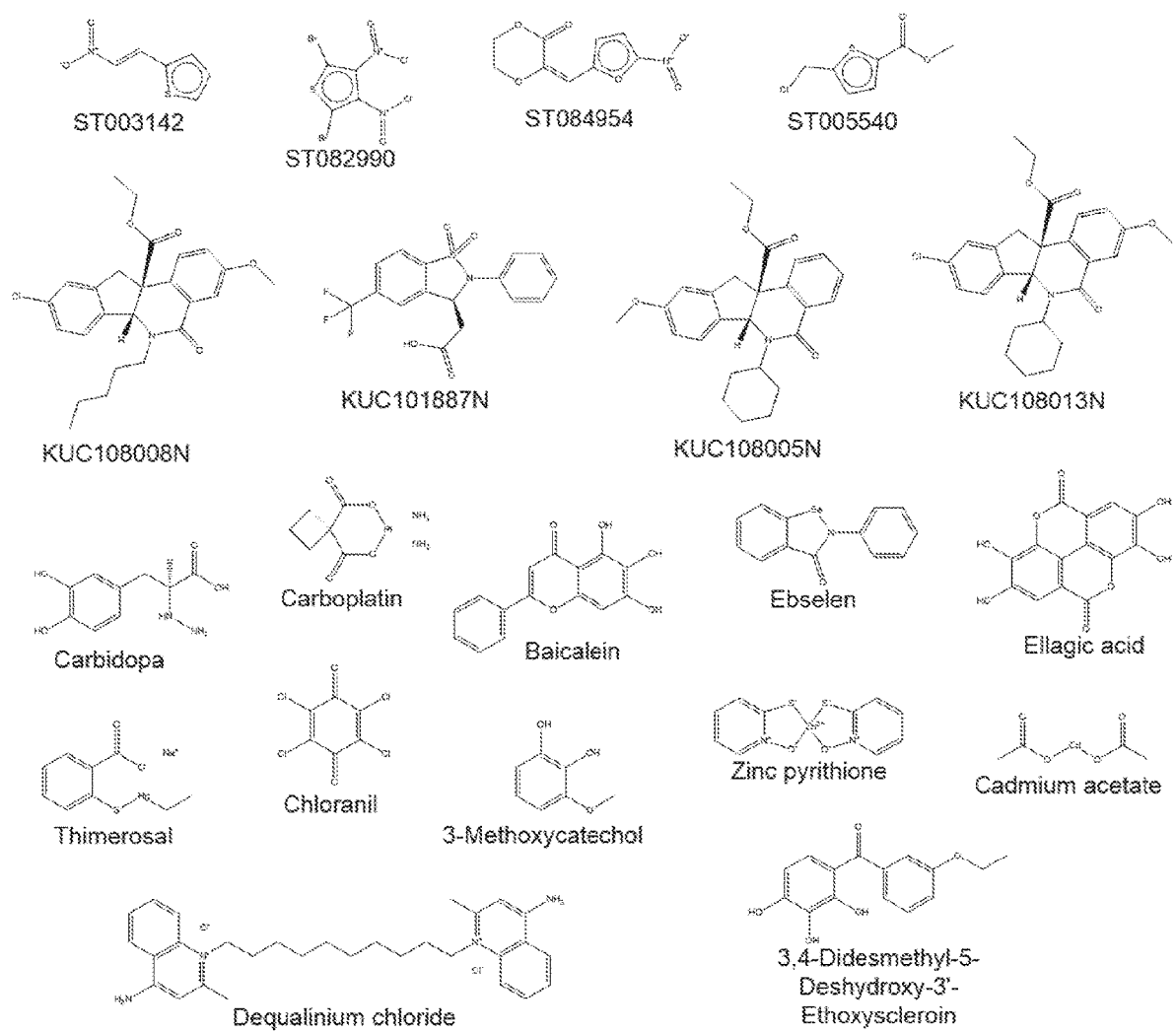

From the compounds that inhibited >30%, 20 were selected for secondary screening and purchased from commercial vendors or supplied by the University of Kansas (KU CMLD) in powder form. Compounds were selected based on availability and structure; all 20 compounds are depicted with their common name and structure in FIG. 5. Secondary screening assays were performed that evaluate FeEnt transport via an alternative measure and also assays to monitor other TonB-dependent processes, i.e., other transporters besides FepA. Specifically, siderophore nutrition tests were used for FeEnt and Fc transport (transported by FhuA) and colicin B (FepA) and colicin Ia (Cir) killing tests (Table 3).

For siderophore nutrition tests, OKN3+pITS23 bacteria were iron-starved and then plated in top agar with either FeEnt or Fc as an iron source placed on a disc in the center of the agar. Each compound at 100 µM or the control CCCP (15 µM or 20 µM) was added to the bacteria prior to siderophore exposure. Siderophore utilization resulted in a tight growth halo surrounding the siderophore-containing disc, and compounds that resulted in a greater than 5% increase in growth halo diameter or prevention of halo formation were considered inhibitors (Table 3, FIG. 6A). Baicalein and ellagic acid resulted in two unique halos and were therefore considered inhibitors as well although the phenotype remains to be further investigated.

TABLE 3

Secondary screening of top 20 candidate compounds against E. coli and A. baumannii.

| | E. coli | | | | A. baumannii | |
| --- | --- | --- | --- | --- | --- | --- |
| Treatment | FeEnt Halo (cm)* | Fc Halo (cm)* | % Colicin B killing‡ | MIC (µM)** | FeEnt Halo (cm)* | MIC (µM)** |
| Untreated | 1.45 ± 0.123 | 1.54 ± 0.105 | 98.34 ± 2.38 | n/a | 1.16 ± 0.065 | n/a |
| KUC101887N | 1.42 ± 0.076 | 1.53 ± 0.072 | 99.2 ± 0.86 | — | 1.11 ± 0.051 | — |
| KUC108008N | 1.48 ± 0.029 | 1.59 ± 0.036 | 100 ± 0.00 | — | 1.08 ± 0.029 | — |
| KUC108005N | 1.48 ± 0.058 | 1.58 ± 0.058 | 97.5 ± 1.38 | — | 1.11 ± 0.038 | — |
| KUC108013N | 1.46 ± 0.064 | 1.63 ± 0.058 | 100 ± 0.00 | — | 1.12 ± 0.035 | — |
| ST003142 | 2.72 ± 0.325 | 2.07 ± 0.029 | 15.6 ± 4.16 | 256 | 1.67 ± 0.350 | 512 |
| ST005540 | 1.62 ± 0.165 | 1.71 ± 0.170 | 99.0 ± 0.67 | — | 1.13 ± 0.025 | — |
| ST082990 | 0 | 0 | 99.3 ± 0.67 | 128 | 0 | 16 |
| ST084954 | 0 | 0 | 99.3 ± 0.73 | 32 | 1.35 ± 0.116 | 256 |
| Carbidopa | 1.58 ± 0.089 | 1.65 ± 0.055 | 96.0 ± 2.0 | — | 1.10 ± 0.015 | — |
| Carboplatin | 1.54 ± 0.031 | 1.62 ± 0.015 | 100 ± 0.00 | — | 1.10 ± 0.050 | — |
| Baicalein | 1.65 ± 0.050 | 1.65 ± 0.045 | 54.6 ± 13.2 | — | 1.23 ± 0.098 | — |
| Ebselen | 0 | 0 | 93.4 ± 2.25 | 128 | 0 | 32 |
| Ellagic acid | 1.61 ± 0.075 | 1.36 ± 0.197 | 82.9 ± 3.75 | — | 1.08 ± 0.041 | 256 |
| Dequalinium Chloride | 1.43 ± 0.110 | 1.55 ± 0.131 | 98.7 ± 1.10 | — | 1.14 ± 0.017 | — |
| 3-Methoxycatechol | 1.50 ± 0.100 | 1.60 ± 0.500 | 98.2 ± 2.27 | — | 1.12 ± 0.025 | — |
| P-Chloranil | 1.51 ± 0.148 | 1.57 ± 0.059 | 93.0 ± 3.36 | — | 1.14 ± 0.015 | — |
| DDES | 1.59 ± 0.170 | 1.69 ± 0.177 | 98.0 ± 1.24 | — | 1.18 ± 0.028 | — |
| Thimerosal | 0 | 0 | 98.6 ± 0.98 | 2 | 0 | 1 |
| Cadmium acetate | 2.22 ± 0.076 | 2.08 ± 0.42 | 98.4 ± 0.43 | 512 | 0 | 256 |
| Zinc pyrithione | 0 | 0 | 20.4 ± 5.90 | 4 | 0 | 16 |
| 120304 | 1.60 ± 0.100 | 1.57 ± 0.072 | 98.4 ± 0.68 | — | NT | NT |

*Siderophore nutrition test using OKN3 + pITS23 with 50 µM FeEnt or Fc with 100 µM compound in DMSO.
‡Colicin B killing assay showing percent killing of MG1655 by ColB in the presence of compound in DMSO; compound alone killed ≤10% under these conditions.
**MIC determined by testing titration of compounds in DMSO against MG1655 or 17978 in LB. Concentration equals the minimal concentration where inhibition was observed from a two-fold dilutions of 0.5-512 µM compound. If MIC >512 µM, value not listed.
NT = not tested.

Colicins are a type of bacteriocins that are toxic to various species of E. coli, including MG1655 and derivative OKN3, some of which require TonB for translocation across outer membrane receptors. Colicin B and colicin Ia are transported by FepA and Cir, respectively, but both require TonB for transport. Therefore, colicin killing of E. coli MG1655 and OKN3+pITS23 was tested by iron-starving the bacteria, followed by incubating with sub-toxic concentrations of compound, DMSO, or CCCP, and plated on LB agar in the presence of colicin B or Ia in order to determine the percent killing. Compounds that prevented killing by greater than 5% and resulted in increased bacterial survival in the presence of colicin were considered inhibitors (Table 3, FIG. 6B). Compounds that displayed inhibition in all three of the three secondary screens (FeEnt utilization, Fc utilization, and ColB killing) were ST003142, baicalein, ebselen, thimerosal, and zinc pyrithione, and were considered authentic TonB inhibitors. Compounds that were inhibitory in two of the three secondary assays, ST082990, ST084954, ST005540, cadmium acetate, and ellagic acid also have potential as TonB inhibitors of FeEnt transport.

In order to evaluate general bactericidal activity of the 20 candidate inhibitors, we grew MG1655 in the presence of a two-fold dilution series of compound in LB and calculated the effective MIC up to 512 μM (Table 3). "Authentic" TonB inhibitors ST003142, ebselen, thimerosal, and zinc pyrithione, and "possible" TonB inhibitors ST082990, ST084954, cadmium acetate had detectible MICs≤512 μM. Overall this proof-of-concept HTS yielded at least 5-9 compounds that inhibit TonB-mediated transport in $E.$ $coli$ and may be effective therapeutic targets against Gram-negative pathogens.

Compounds active against $E.$ $coli$ were active were then tested to determine their activity against other Gram-negative bacterial, notably pathogens for which new antimicrobials are needed, such as $A.$ $baumannii$. For these experiments, 20 compounds were used in secondary screening in $E.$ $coli$ against $A.$ $baumannii$ via FeEnt siderophore nutrition tests and MICs in LB (Table 3). The compounds that inhibited $E.$ $coli$ growth and FeEnt transport likewise inhibited $A.$ $baumannii$, but with differences in sensitivity. For example, some compounds had higher or lower MICs against $A.$ $baumannii$ compared to $E.$ $coli$. These results give precedence that performing a similar HTS screen is a viable possibility for the identification of compounds that inhibit $A.$ $baumannii$ TonB-dependent transport.

$A.$ $baumannii$ encodes FepA that transports FeEnt. Considering the success of the proof-of-concept HTS in $E.$ $coli$ and the activity of compounds against $A.$ $baumannii$, the fluorescence assay was adapted to $A.$ $baumannii$. $A.$ $baumannii$ ATCC 17878 is predicted to encode FepA from A1S_0980 and A1S_0981, split by a stop codon. PCR analysis of genomic DNA at the loci juncture revealed that in fact the annotated stop codon is absent and therefore A1S_0980 and A1S_0981 represent one open reading frame (ORF, data not shown). This ORF was deleted from the chromosome, resulting in ΔfepA, which was evaluated for utilization of FeEnt by $A.$ $baumannii$.

First, WT $A.$ $baumannii$ and ΔfepA was grown in MOPS minimal media plus or minus apoferrichrome A, a siderophore not utilized by $A.$ $baumannii$ which acts as a highly specific iron chelator (FIG. 7A). In both iron-starved conditions, ΔfepA grew comparably to WT, suggesting that other iron acquisition system systems are sufficient for $A.$ $baumannii$ growth in the absence of FepA. However, iron-starved ΔfepA displays a significant growth defect when FeEnt is the sole iron source, suggesting that AbaFepA does in fact contribute to FeEnt consumption by $A.$ $baumannii$ (FIG. 7B). Moreover, when iron-starved WT $A.$ $baumannii$ and ΔfepA are evaluated by siderophore nutrition test for FeEnt and Fc, ΔfepA cannot utilize FeEnt but is uninhibited for Fc utilization when compared to WT (FIG. 7C). The inability to utilize FeEnt is restored following expression of AbaFepA in trans under its native promoter (pfepA) or exogenous promoter (p2682profepA) (FIG. 7D).

To directly evaluate FeEnt transport by AbaFepA, $^{59}$FeEnt accumulation was measured over 45 min using 1 μM $^{59}$FeEnt in WT $A.$ $baumannii$, ΔfepA, and the complementation strain (FIG. 7E). Whereas WT and the complementation strain can accumulate 500-600 pM FeEnt per 1×10$^9$ cells by 45 min, ΔfepA accumulates essentially no FeEnt, confirming that AbaFepA is the transport mechanism for FeEnt. $^{59}$FeEnt uptake was also measured over a range of FeEnt concentrations up to 100 nM at 2 min by WT $A.$ $baumannii$ and ΔfepA (FIG. 7F). Overall, these data show that WT $A.$ $baumannii$ FepA and plasmid-expressed AbaFepA in ΔfepA can transport and utilize FeEnt as an iron source.

Generation of Cys Substitution Mutants in $A.$ $baumannii$ FepA.

Figure 8:
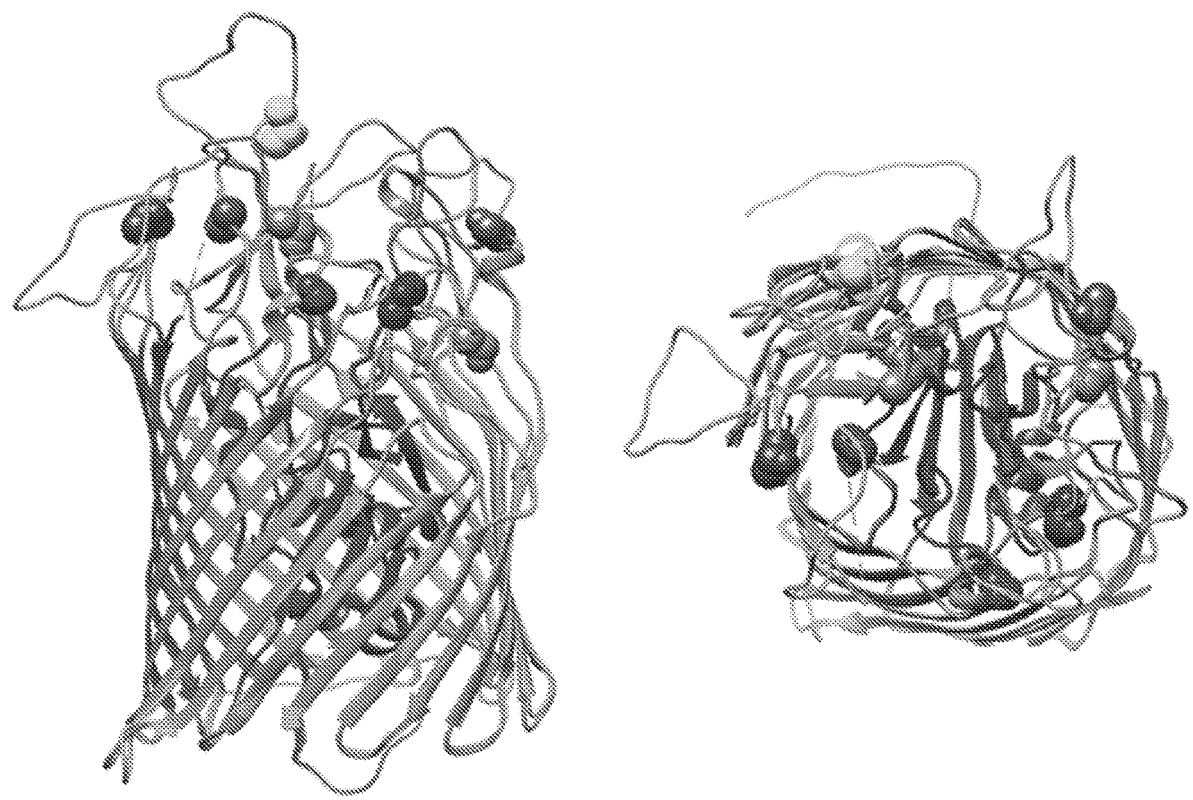
Figure 9:
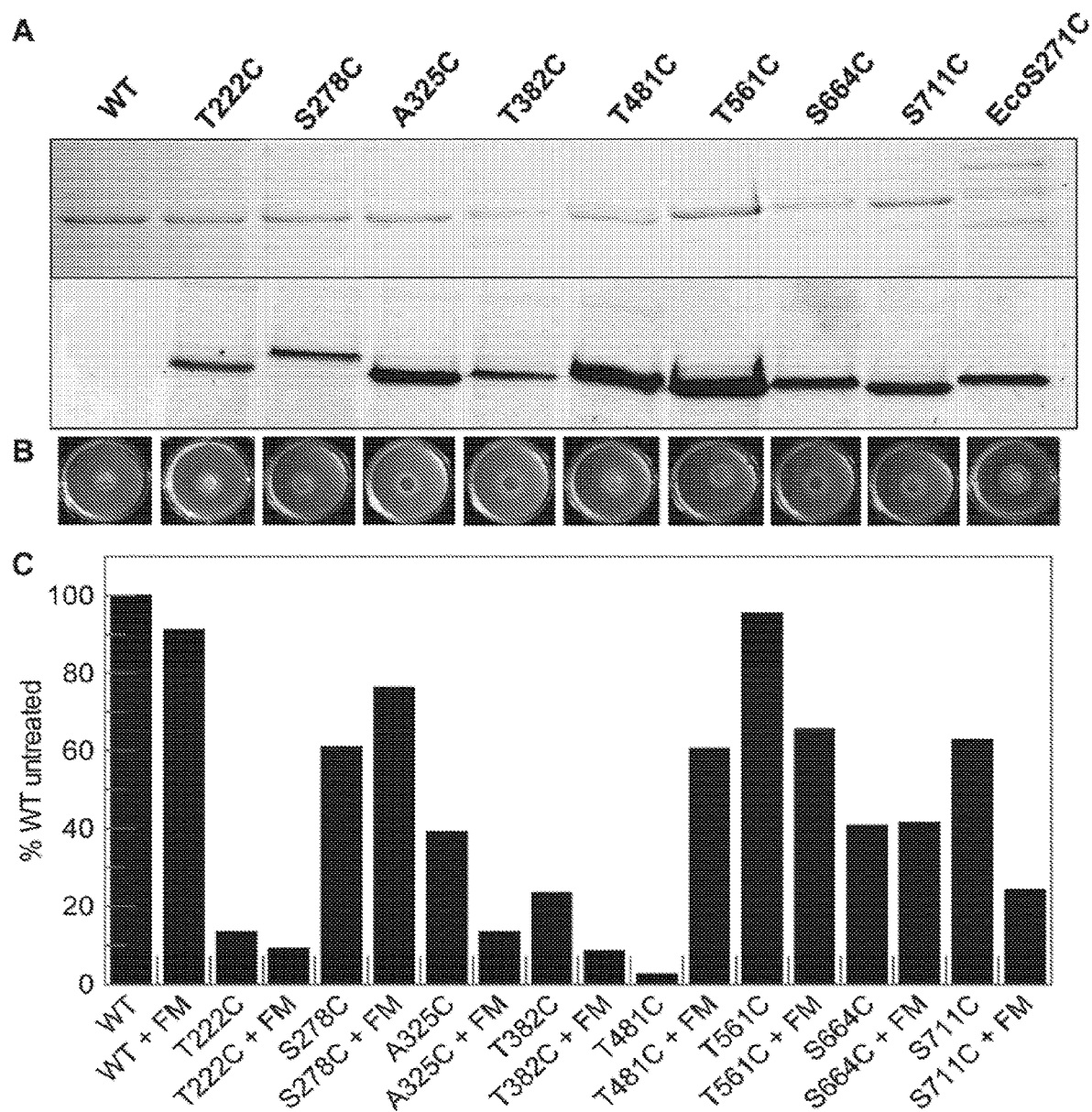

The generation of Cys substitutions in the outer loops of AbaFepA requires knowledge regarding the structure of the protein. Since there is no crystal structure of AbaFepA, the amino acid sequence of AbaFepA was threaded against the crystal structure of EcoFepA in order to generate a predictive structural model of AbaFepA (FIG. 8). From this predicted structure, nine amino acids targets were identified for Cys substitution in varying outer loops of AbaFepA, guided by past Cys substitutions made in loops of EcoFepA. Site-directed mutagenesis was then carried out on AbaFepA (pfepA) at the selected amino acids substituting to Cys: T222C, S278C, A325C, T382C, T481C, T561C, S664C, and S711C (FIG. 8). Each mutant FepA was expressed in ΔfepA, labeled with FM, and evaluated for Cys-specific labeling by SDS-PAGE and fluorescent imaging (FIG. 9A). All mutants were labeled similar to EcoFepA-S271C, albeit to varying degrees, while WT AbaFepA showed no labeling. The ability of each mutant FepA to utilize FeEnt was tested by siderophore nutrition test, which all mutants transported similarly to WT AbaFepA and EcoFepA-S271C (FIG. 9B). In order to use a labeled Cys mutant for monitoring FeEnt transport, the labeled cells must retain significant activity in FeEnt transport. Thus, $^{59}$FeEnt uptake of each mutant was measured prior to and after FM labeling by Vmax screening, which revealed a wide range of functionality across mutants. Following comparison to unlabeled WT AbaFepA cells (FIG. 9C), three mutants were identified that had greater than 30% transport compared to WT: S278C, T561C, and S664C. In total, nine functional AbaFepA mutants were generated, of which at least three represent possible candidates for use in the fluorescence assay of FeEnt transport.

Fluorescence Assay for FeEnt Transport Using $A.$ $baumannii$ FepA Cys Mutants.

Despite differences in the $^{59}$FeEnt transport by labeled $A.$ $baumannii$ cells expressing the AbaFepA Cys mutants compared to WT, all nine Cys substitution mutants were assessed along with WT AbaFepA in the SLM fluorescence assay for FeEnt transport using 10 nM FeEnt (FIG. 10A). Consistent with the FM-labeling and SDS-PAGE experiments, WT AbaFepA had overall fluorescence volts at least 50% or lower compared to Cys substitution mutant fluorescence volts (FIG. 11A) and did not result in any detectable fluorescence quenching or recovery (FIG. 11B). Of all the mutants, only S278C, S664C, and T561C displayed significant quenching and recovery of fluorescence following addition of FeEnt. S278C and S664C quenched to similar levels following addition of FeEnt, 10-12% compared to initial fluorescence, and T561C quenched the most at 82-85% of initial fluorescence. While all three strains recovered completely, the time scale for S664C and T561C was greater than 1000 s, whereas S278C recovered by 600 s. Since the S278C mutant recovered the quickest of the three mutant strains, it was used to better define the dose-dependency of the fluorescence quenching and recovery using 5, 10, 15, 20 or 40 nM FeEnt (FIG. 10B). In fact, 20 nM appears to be an ideal concentration of FeEnt for maximum quenching with complete recovery by cells by 600 s. Lastly, the impact of the energy poison CCCP on FeEnt transport by AbaFepA-S278C was tested (FIG. 10C). $A.$ $baumannii$ is strikingly more sensitive to CCCP compared to $E.$ $coli$ where 5 M CCCP completely inhibits FeEnt transport by AbaFepA. The ability of frozen FM-labeled *A. baumannii* cells to be used in the fluorescence assay was also evaluated, as done for *E. coli*. The results demonstrate that frozen, labeled ΔfepA+pfepA-5278C cells are viable and perform in the assay with a reasonable recovery time of 1000 s (FIG. 11C).

Figure 12:
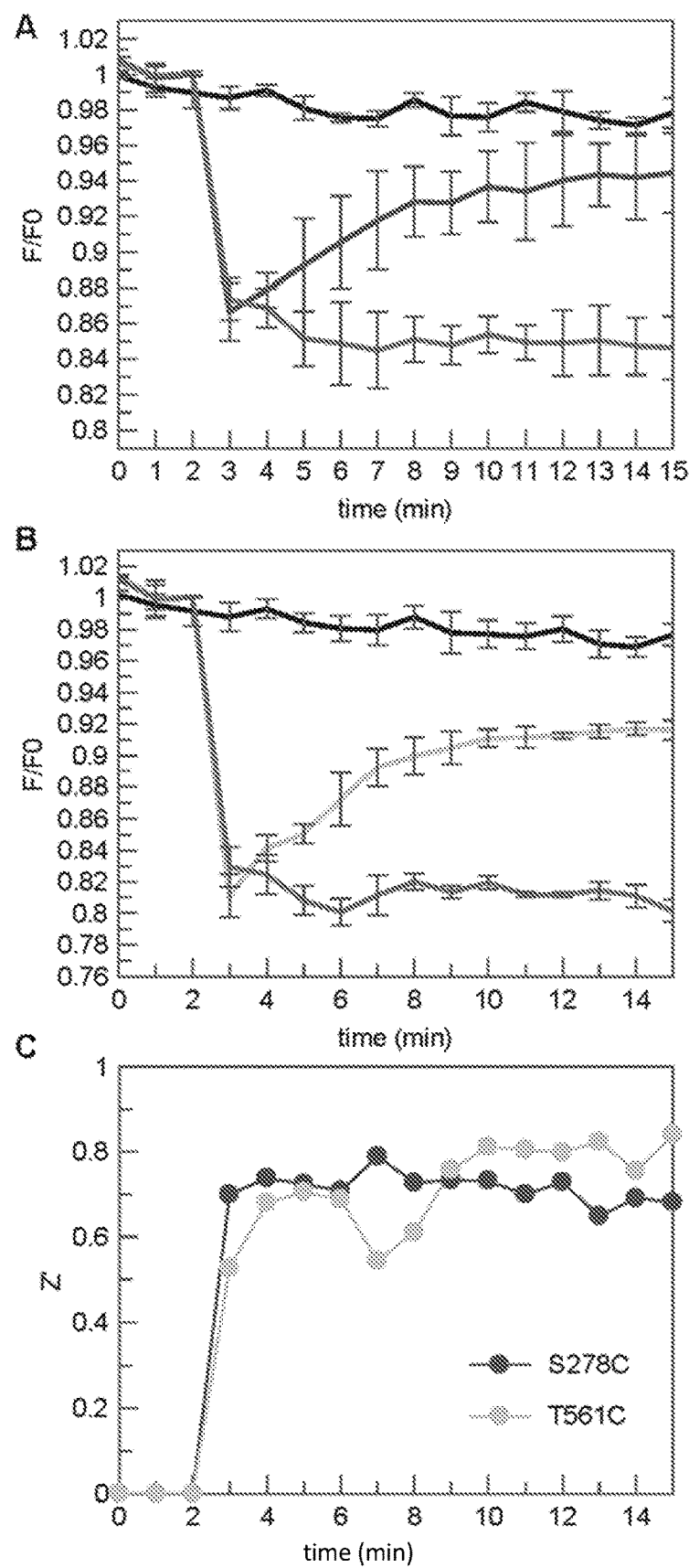

The *A. baumannii* fluorescence assay was also adapted to HTS format as done for *E. coli*. The three best performing mutants in the SLM experiments, S278C, S664C, and T561C were evaluated for FeEnt transport in a 96-well plates (FIG. 12). Preliminary experiments showed that 20 nM FeEnt and a cell dilution 1:10 was optimal for 96-well format and moreover, S664C did not demonstrate any recovery following FeEnt treatment. However, both S278C and T561C mutants performed well in the 96-well plate format with 86% and 82% recovery, respectively, and near complete recovery (FIG. 12 A, B). Both mutants also had Z' factors between 0.6-0.8 in the range of time points (8-15 min) that would be evaluated in HTS for inhibitors of transport, i.e. fluorescence recovery (FIG. 12C). Together these results demonstrate effective application of the fluorescence assay to HTS for *A. baumannii* and potential for performing an HTS for inhibitors of *A. baumannii* TonB-dependent transport.

C. Discussion

TonB-dependent transport is a process required for the acquisition of iron and other nutrients by Gram-negative bacteria. Therefore, identification of inhibitors of TonB-dependent transport has implications in both tool discovery for understanding TonB function as well as chemical compounds that may be used for antimicrobial drug development. A proof-of-concept, fluorescence-based HTS in *E. coli* was performed, which yielded at least 7 compounds with activity against *E. coli* and *A. baumannii* TonB-dependent transport. Moreover, we transferred the fluorescence assay into *A. baumannii*, using AbaFepA and FeEnt and demonstrated its efficacy in the HTS format. Assay transfer into *A. baumannii* also uncovered fundamental aspects of *A. baumannii* iron acquisition mechanisms.

In order to investigate various compounds as potential TonB inhibitors, a proof-of-concept HTS in *E. coli* was carried out in microplates using the invented fluorescence based assay that monitors FeEnt transport by FepA (a TonB-dependent process). The HTS screening assay had a Z' factor across plates equal to 0.87 (FIG. 4), which statistically validates the quality performance of the HTS. The screen libraries encompassed over 17,000 compounds and yielded a hit rate of 0.54%, which together with the Z' factor, demonstrates efficacy of the screen (Table 2). Secondary screening of 20 of the 95 "hits" from the primary screen was performed using two different assays and revealed at least 5 out of the 20 compounds are authentic TonB inhibitors (Table 2, FIGS. 5, 6). With 25% of the 20 compounds subjected to secondary screens, if the remaining 75 compounds were tested, it is likely that up to an additional 19 inhibitory compounds would be identified (25% of 75 remaining hits). If these numbers are extrapolated to the larger HTS, then 0.135% (25% of 0.54% hit rate) of HTS hits represent authentic TonB inhibitors, which is 24 out of 17,441 screened compounds in the screen. Considering that following identification, very few compounds are carried through the drug development process, performance of a larger scale screen would be more efficacious to identify a compound with true therapeutic potential, earlier in the overall process.

Figure 6:
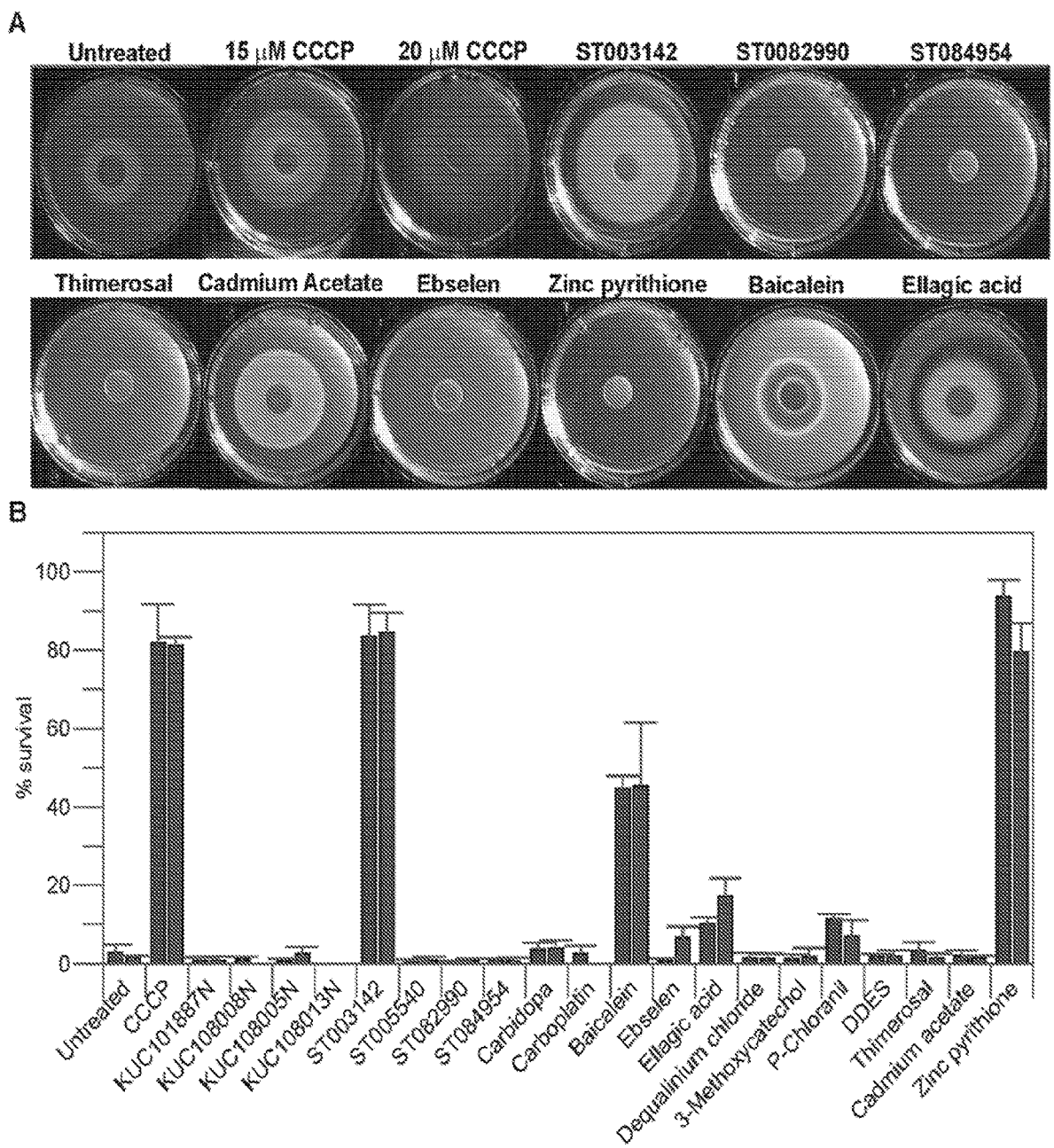

Secondary screening also revealed some unique phenotypes for some compounds that may be useful in developing tools to study FepA function. First, baicalein and ellagic acid had growth halos distinct from each other and all of the other compounds (FIG. 6A). While explanations require further study, it suggests that these compounds uniquely impact siderophore transport. Secondly, there were several compounds that differentially impacted transport of FeEnt, Fc, and ColB. For example, ST082990, ST084954, ST005540 all inhibited FeEnt and Fc transport but not ColB (Table 3, FIG. 6). This would suggest that their activity is specific to siderophore but not colicin transport. On the other hand, P-chloranil inhibited ColB but not FeEnt or Fc transport. Compounds such as these could provide unique tools to studying transport of specific molecules by FepA and teasing out FepA transport mechanism.

Figure 7:
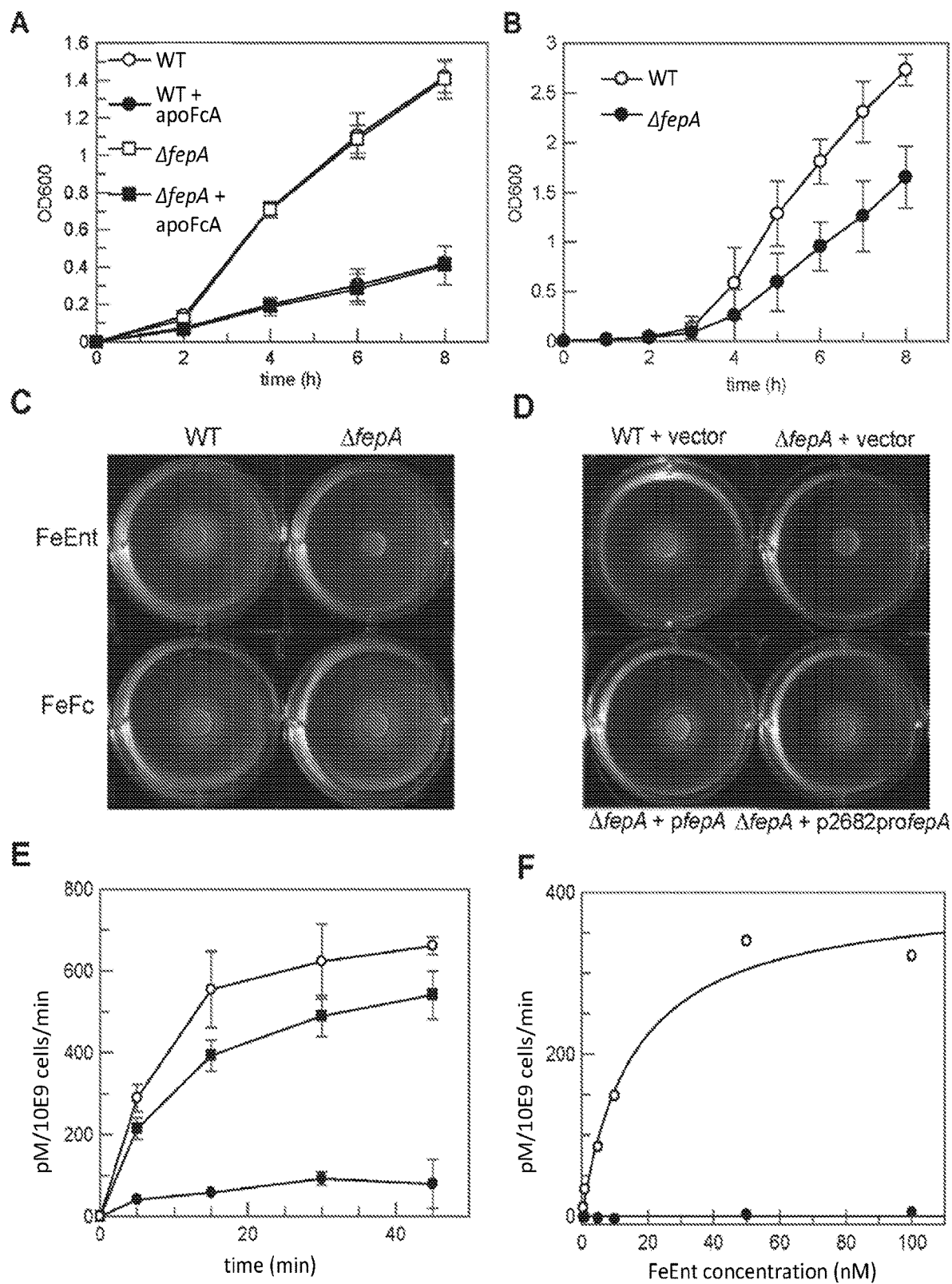

*A. baumannii* 17978 encodes at least three siderophore systems that are up-regulated in a low iron environment. Nevertheless, *A. baumannii* also encodes OM receptors for siderophores that it does not synthesize, such as FhuA, FhuE, and FepA, which are up-regulated in iron-limiting conditions, possibly via Fur. The data demonstrates that A1S_0980 A1S_0981 represents one ORF encoding FepA in *A. baumannii* 17978 and that AbaFepA can transport FeEnt (FIG. 7 B-F). While AbaFepA is not required for growth in iron-starved conditions (FIG. 7A), it is utilized when FeEnt is the sole iron source (FIG. 7 B-D). These data suggest that generally *A. baumannii* can adapt to iron starvation by relying on other siderophores and iron acquisition systems. However, AbaFepA may serve a role in only situations of extreme iron starvation or in environments where FeEnt-secreting organisms are present, such as during a co-infection or polymicrobial communities. Further studies are required for better understanding of AbaFepA function regarding its role in iron acquisition, as well as for other predicted exogenous siderophore transporters.

To design Cys into the outer loops of AbaFepA, a model of AbaFepA was first created by threading the secondary sequence against the crystal structure of EcoFepA using the program Chimera. There was significant homology between the proteins, with the predominate variations being found in the N-terminal sequence and the physical location of the loops. However, there was enough homology to predict amino acids in the outer loops for Cys substitution (FIG. 8). AbaFepA contains only two Cys located in the interior of the OM channel that, similar to EcoFepA, likely form disulfide bonds. Labeling conditions were used to minimize non-specific labeling of Lys residues so that labeling with FM would be specific to the engineered Cys residues. Fortunately, there was minimal background labeling in the WT or mutant strains. In addition, no mutation itself grossly impacted the ability of AbaFepA to utilize FeEnt (FIG. 9A, B). Differences in FeEnt transport by labeled and even unlabeled mutants proteins could be explained by either the Cys or the fluorophore interfering with FeEnt binding or impairment of conformational plasticity required for transport (FIG. 9C). It is likely that selection of additional amino acids for Cys modification in AbaFepA loops would ultimately generate a mutant that has decreased impact on FeEnt transport following labeling or performs better in the fluorescence assays. Overall, the labeling procedure was sufficient to specifically label the engineered Cys residues in the outer loops of AbaFepA with high specificity and little impact on AbaFepA function. Moreover, the data on *E. coli* in combination with confirmation of this approach in *A. baumannii*, suggest that the same strategy could be applied to other Gram-negative organisms encoding FepA.

Figure 10:
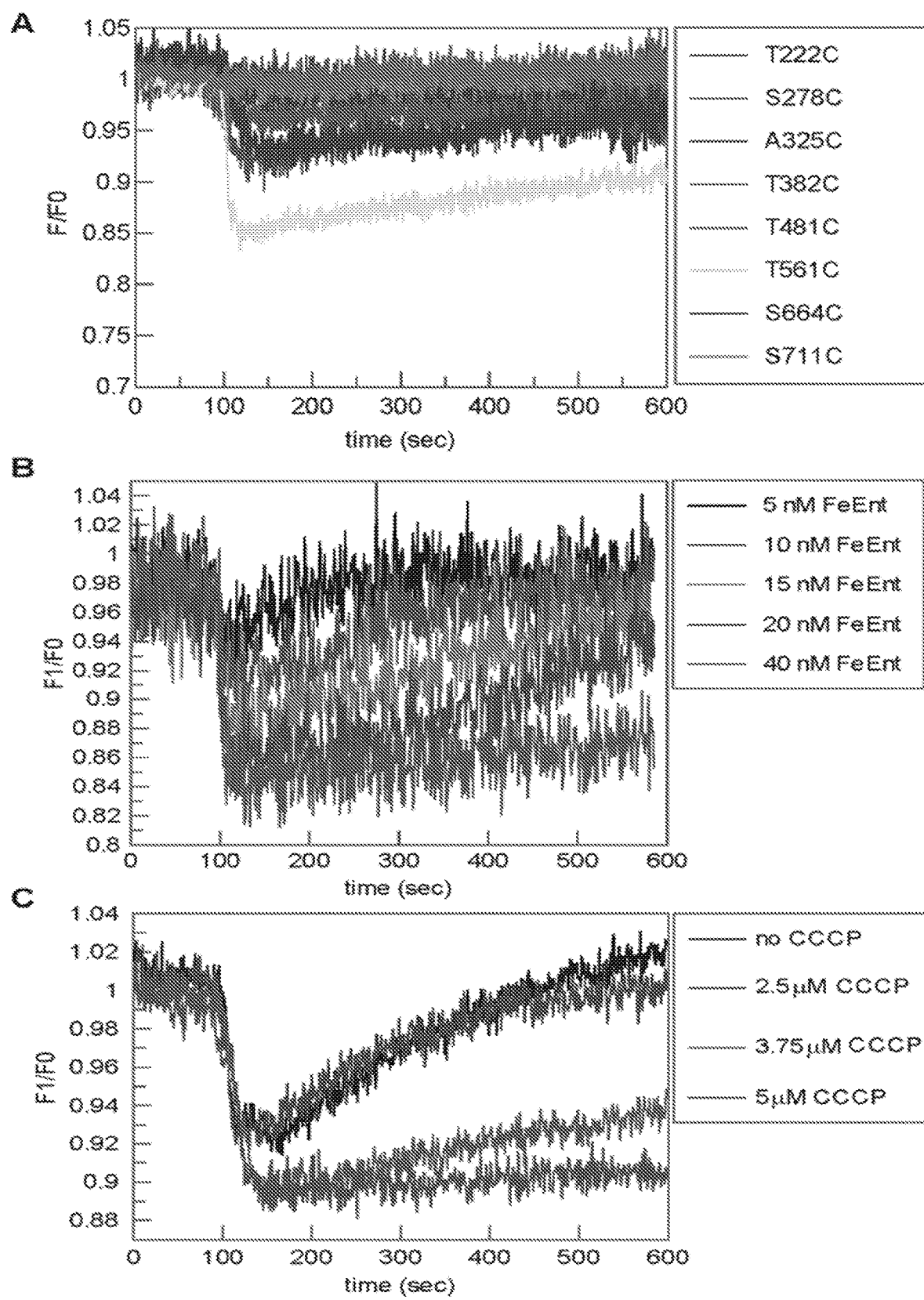
Figure 11:
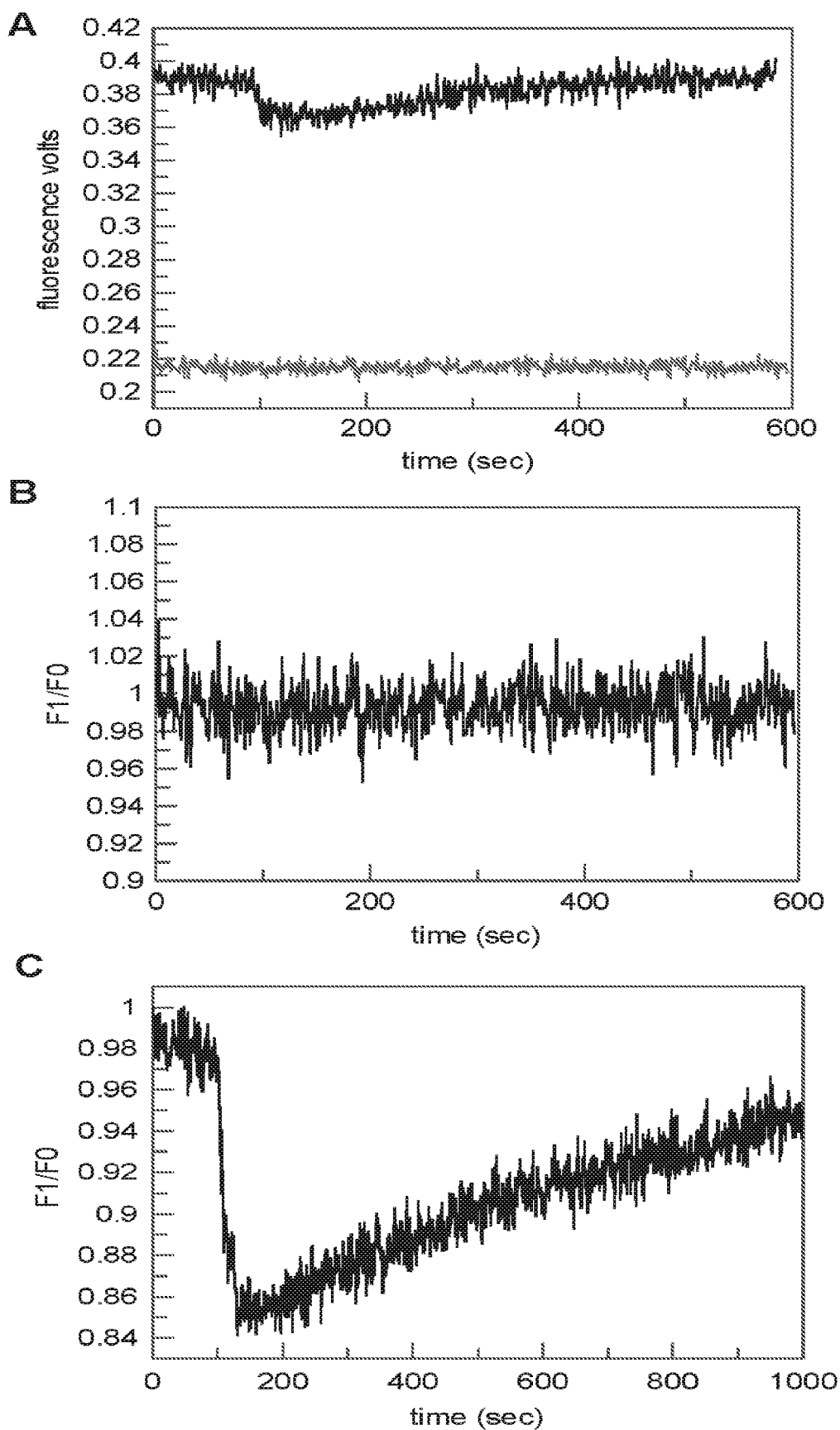
Figure 13:
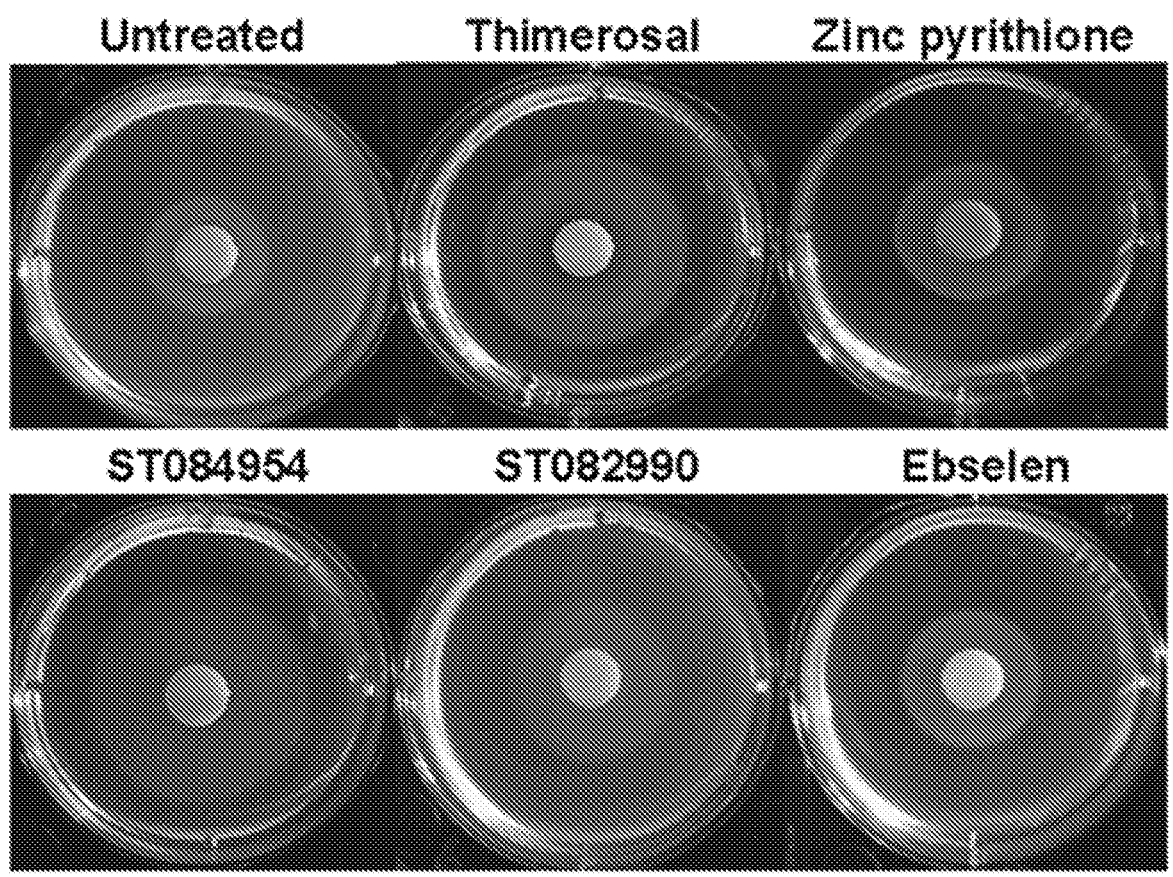

The fluorescence assay in *A. baumannii* worked very similarly as for *E. coli*, with the main difference being in the percent quenching following addition of FeEnt to the cells (FIG. 10). While the maximum fluorescence quenching observed with current AbaFepA mutants is 20%, EcoFepA, quenched as low as 40%. It is possible that this is due to hindrance by the LPS or capsule of *A. baumannii*, which limits the extent of conformational change in the loops containing the FM-labeled Cys, thereby reducing the magnitude of quenching. If LPS or capsule are determined to be responsible for constraining quenching levels, then this limitation could be reduced using either an LPS or capsule mutant in *A. baumannii*. However, despite the perceived limits on percent quenching, the assay still achieved dose-dependent quenching and recovery by AbaFepA Cys mutants to levels adequate for HTS format (FIG. 12). Additionally, the fluorescence assays could be carried out for both *E. coli* and *A. baumannii* using cells that were labeled, frozen, and thawed, which is an advantage to using the same batch of cells for an entire HTS (FIGS. 3, 13). Of note, for application to bacteria with deficient genetic tools, the fluorescence assay was able to be performed in WT *A. baumannii* expressing the Cys mutations (data not shown), suggesting that the inability to eliminate fepA from the chromosome does not exclude the employment of this fluorescence assay.

In summary, these examples demonstrate a fluorescence-based assay for measurement of FeEnt transport by FepA, which applies to the HTS format and allows for the identification of TonB inhibitors. Following an HTS in *E. coli* using this assay and following secondary screening procedures, at least five compounds were identified herein with activity against TonB function. Moreover, this assay can be applied to other Gram-negative bacteria, as confirmed for *A. baumannii* and could serve as a valuable tool to identify mechanistic tools and therapeutic agents related to TonB function.

We claim:

1. A cell-based assay for identifying a compound that inhibits TonB-dependent iron transport in Gram-negative bacteria, said assay comprising:
    creating a reaction solution by contacting a candidate compound with Gram-negative bacteria in the presence of iron for a sufficient period of time, wherein said Gram-negative bacteria is engineered with a detectable label, wherein said engineered Gram-negative bacteria comprises a FepA protein on its outer membrane comprising an amino acid residue that has been engineered with said detectable label that generates a detectable signal, said engineered Gram-negative bacteria having native iron transport capabilities;
    exposing said reaction solution to an energy source to generate said detectable signal; and
    detecting changes in the detectable signal in the reaction solution over time, wherein said changes correspond to the effect of said candidate compound on TonB-dependent iron transport in said Gram-negative bacteria.

2. The assay of claim 1, wherein said FepA protein is substituted with a cysteine residue, wherein said detectable label is a fluorophore attached to said cysteine residue.

3. The assay of claim 2, wherein said fluorophore is fluorescein maleimide.

4. The assay of claim 1, wherein said engineered Gram-negative bacteria is selected from the group consisting of *Acinetobacter baumannii, Klebsiella pneumoniae, Pseudomonas aeruginosa, Enterobacter aerogenes,* and *Escherichia coli*.

5. The assay of claim 1, wherein the concentration of engineered Gram-negative bacteria in said reaction solution is from about $5 \times 10^6$ to about $3 \times 10^7$ cells/ml.

6. The assay of claim 1, wherein said reaction solution comprises an aqueous solution and at least one nutrient to support cell function of said bacteria.

7. The assay of claim 1, wherein said creating a reaction solution comprises:
    contacting said candidate compound with said engineered Gram-negative bacteria in a reaction vessel;
    adding a source of iron to said reaction vessel; and
    incubating said candidate compound with said engineered Gram-negative bacteria and source of iron for a period of time.

8. The assay of claim 7, wherein said reaction solution has a total volume of less than about 300 µL total solution.

9. The assay of claim 7, wherein said source of iron is ferric enterobactin.

10. The assay of claim 9, wherein from about 5 to about 20 nM ferric enterobactin in solution is added to the reaction vessel.

11. The assay of claim 7, said assay comprising a first reading comprising:
    exposing said reaction solution to said energy source to generate said detectable signal before adding said source of iron; and
    detecting an initial detectable signal.

12. The assay of claim 11, said assay further comprising a second reading comprising:
    exposing said reaction solution to said energy source to generate said detectable signal immediately after adding said source of iron; and
    detecting an intermediate detectable signal, wherein a decrease in intensity of said intermediate detectable signal as compared to said initial detectable signal indicates binding of iron to said FepA protein.

13. The assay of claim 12, wherein said second reading is carried out from about 1 second to about 120 seconds after adding said source of iron to said reaction vessel.

14. The assay of claim 11, said assay further comprising a third reading comprising:
    exposing said reaction solution to said energy source to generate said detectable signal at least 5 minutes after adding said source of iron to said reaction vessel; and
    detecting a final detectable signal, wherein an increase in intensity of said final detectable signal as compared to said intermediate detectable signal indicates transport of said iron by said FepA protein, and wherein a lack of increase in intensity of said final detectable signal as compared to said intermediate detectable signal indicates inhibition of said TonB-dependent iron transport by said candidate compound.

15. The assay of claim 1, wherein said engineered Gram-negative bacteria are cryopreserved cells, said assay further comprising thawing said cryopreserved cells, and washing said cells to remove any cryoprotectant before creating said reaction solution.

16. The assay of claim 1, wherein said assay is a high-throughput screening method, further comprising distributing said reaction solution into a plurality of individual reaction vessels, each vessel comprising respective reaction volumes.

17. The assay of claim 16, wherein said distributing comprises:
    depositing said engineered Gram-negative bacteria in an aqueous solution in a reaction vessel;
    adding said candidate compound to said reaction vessel;

adding a source of iron to said reaction vessel; and
incubating said candidate compound with said engineered Gram-negative bacteria and source of iron for a period of time.

18. The assay of claim 16, wherein a plurality of candidate compounds are added to respective reaction vessels.

19. The assay of claim 16, wherein each reaction vessel is a microwell in a multi-compartment microplate.

20. The assay of claim 19, wherein said microplate is a 96-, 384-, or 1536-compartment microplate.

21. The assay of claim 20, wherein all or a subgroup of the microwells in said microplate are monitored simultaneously to detect changes in the detectable signal in respective reaction solutions over time.

22. The assay of claim 1, further comprising a secondary screening step to determine a mechanism of inhibition of said candidate compound.

23. The assay of claim 22, wherein said secondary screening step comprises incubating said engineered-Gram negative bacteria cells with the compound in the presence of a known TonB-dependent bacteriocin.

24. The assay of claim 1, wherein said engineered-Gram negative bacteria cells are live cells.

25. The assay of claim 1, wherein said engineered-Gram negative bacteria is an isolated *Acinetobacter baumannii* comprising a genetically-engineered cysteine substitution in its FepA protein at residue 278, 561, or 664, and a fluorophore covalently attached to the substituted cysteine residue.

* * * * *